(12) United States Patent
Dasseux et al.

(10) Patent No.: US 6,680,203 B2
(45) Date of Patent: Jan. 20, 2004

(54) FOURIER TRANSFORM MASS SPECTROMETRY OF COMPLEX BIOLOGICAL SAMPLES

(75) Inventors: Jean-Louis H. Dasseux, Brighton, MI (US); Roger S. Newton, Ann Arbor, MI (US); Thomas J. Rea, Pinckney, MI (US); Charles L. Bisgaier, Ann Arbor, MI (US); Michael E. Pape, Ann Arbor, MI (US)

(73) Assignee: Esperion Therapeutics, Inc., Ann Arbor, MI (US)

( * ) Notice: Subject to any disclaimer, the term of this patent is extended or adjusted under 35 U.S.C. 154(b) by 118 days.

(21) Appl. No.: 09/735,707

(22) Filed: Dec. 12, 2000

(65) Prior Publication Data

US 2002/0019023 A1 Feb. 14, 2002

Related U.S. Application Data

(60) Provisional application No. 60/217,663, filed on Jul. 10, 2000.

(51) Int. Cl.[7] .............................................. G01N 33/00
(52) U.S. Cl. ........................ 436/86; 436/173; 436/501; 436/503
(58) Field of Search .................................... 436/86, 173

(56) References Cited

U.S. PATENT DOCUMENTS

| | | | |
|---|---|---|---|
| 4,224,031 A | | 9/1980 | Mee et al. |
| 5,770,367 A | * | 6/1998 | Southern et al. ............... 435/6 |
| 6,177,266 B1 | * | 1/2001 | Krishnamurthy et al. 435/173.1 |
| 6,183,950 B1 | * | 2/2001 | Madonna et al. ............... 435/5 |
| 6,207,370 B1 | * | 3/2001 | Little et al. ..................... 435/6 |
| 6,329,146 B1 | * | 12/2001 | Crooke et al. ................. 435/6 |

FOREIGN PATENT DOCUMENTS

| | | |
|---|---|---|
| WO | WO 95/25281 | 9/1995 |
| WO | WO 99/46047 | 9/1999 |
| WO | WO 99/57318 | 11/1999 |
| WO | WO 99/58727 | 11/1999 |
| WO | WO 00/03240 | 1/2000 |
| WO | WO 00/29987 | 5/2000 |
| WO | WO 00/48004 A1 * | 8/2000 |

OTHER PUBLICATIONS

Ritchie et al. "An Integrated Approach to Studying Colon Cancer:", (http://www.ki.se/icsb2002/pdf/ICSB_188.pdf.*

Bergquist et al. "Peptide Mapping of Proteins in Human Body Fluids Using Electrospray Ionization Fourier ransform Ion Cyclotron Resonance Mass Spectrometry", Maa Spectrom. Reviews, 2202, v. 21, pp. 2–15.*

Vaidyanathan et al. "Discrimination of Aerobic Endospore-forming Bacteria via Electrospray–Ionization Mass Spectrometry of Whole Cell Suspensions", Anal. Chem. 2001, v. 73, 4134–4144.*

Lewis et al. "Identification of viral mutants by mass spectrometry", Proc. Natl. Acad. Sci., USA, Jul. 1998, v. 95, pp. 8596–8601.*

(List continued on next page.)

*Primary Examiner*—Jill Warden
*Assistant Examiner*—Yelena Gakh
(74) *Attorney, Agent, or Firm*—Pennie & Edmonds LLP

(57) ABSTRACT

The present invention relates to methods for high information content (HIC) analysis or screening of complex biological systems using Fourier transform mass spectrometry (FTMS). The present methods are useful for analyzing complex biological mixtures containing both high molecular weight molecules (e.g., polynucleotides, proteins, polysaccharides) and low molecular weight molecules (e.g., oligonucleotides, peptides, lipids, oligosaccharides, steroid hormones, catabolic and metabolic intermediates) permit the elucidation of molecular differences between complex biological samples, and permit the identification of biologically active molecules (e.g. therapeutically active drugs, etc.).

32 Claims, 18 Drawing Sheets

OTHER PUBLICATIONS

Ryu et al. "Recent Progress in Biomolecular Engineering", Biotechol. Prog. 2000, v. 16, pp. 2–16.*

Bartlett and Pourfarzam, 1999, "Tandem mass spectrometry–13 the potential", J. Inherit. Metab. Dis. 22:568–571.

Blackstock and Weir, 1999, "Proteomics: quantitative and physical mapping of cellular proteins", Trends Biotechnol. 17:121–127.

Budnik et al., 2000, "Benefits of 2.94μm infrared matrixassisted laser desorption/ionization for analysis of labile molecules by Fourier transform mass spectrometry", Rapid Comm. Mass Spectrom. 14:578–584.

Carr and Annan, 1997, "Overview of peptide and protein analysis by mass spectrometry", in: *Current Protocols in Molecular Biology*, Ausubel et al., eds., John Wiley & Sons, Inc., pp. 10.21.

Dainese et al., 1997, "Probing protein function using a combination of gene knockout and proteome analysis by mass spectrometry", Electrophoresis 18:432–442.

Gaillard and Pepin, 1999, "Poisoning by plant material: review of human cases and analytical determination of main toxins by high–performance liquid chromatography–(tandem) mass spectrometry", J. Chromatog. B. Biomed. Sci. Appl. 733:181–229.

Hau et al., 2000, "Determination of the plant growth regulator chlormequat in food by liquid chromatography–electrospray ionisation tandem mass spectrometry", J. Chromatog. 878:77–86.

Heller et al., 1997, "Discovery and analysis of inflammatory disease–related genes using cDNA microarrays", Proc. Natl. Acad. Sci. USA 94:2150–2155.

Hendrickson and Emmett, 1999, "Electrospray ionization Fourier transform ion cyclotron resonance mass spectrometry", Annu. Rev. Phys. Chem. 50:517–536.

Hollenbeck et al., 1999, "Electrospray and MALDI mass spectrometry in the identification of spermicides in criminal investigations", J. Forensic Sci. 44:783–788.

Humphery–Smith et al., 1997, "Proteome research: complementarity and limitations with respect to the RNA and DNA worlds", Electrophoresis 18:1217–1242.

. . . protein mixtures, Electrophoresis 21:1372–1380.

Jensen et al., 1999, "Probing proteomes using capillary isoelectric forming–electrospray ionization Fourier transform ion cyclotron resonance mass spectrometry", Anal. Chem. 71:2076–2084.

Jungblut et al., 1999, "Proteomics in human disease: cancer, heart and infectious diseases", Electrophoresis 20:2100–2110.

Keen and Findlay, 1995, "Protein sequencing techniques", in: *Molecular Biology and Biotechnology*, Robert A. Myers, ed., VCH Publishers, Inc. p. 771–773.

Lashkari et al., 1997, "Yeast microarrays for genome wide parallel genetic and gene expression analysis", Proc. Natl. Acad. Sci. USA 94:13057–13062.

Last and Robinson, 1999, "Protein folding and interactions revealed by mass spectrometry", Curr. Opin. Chem. Biol. 3:564–570.

Li et al., 1999, "Identification of intact proteins in mixtures by alternated capillary liquid chromatography electrospray ionization and LC ESI infrared multiphoton dissociation Fourier transform ion cyclotron resonance mass spectrometry", Anal. Chem. 71:4397–4402.

Liang and Pardee, 1992, "Differential display of eukaryotic messenger RNA by means of the polymerase chain reaction", Science 257:967–971.

McLafferty, 1994, "High–resolution tandem FT mass spectrometry above 10 kDa", Acc. Chem. Res. 27:379–386.

Nakagawa, 2000, "FTMS for proteome analysis", J. Mass Spectrom. Japan 48:207–210 (CA 134:159519).

Nguyen et al., 1995, "Protein mass spectrometry: applications to analytical biotechnology", J. Chromatogr. A 705:21–45.

Palmblad et al., 2000, "Analysis of enzymatically digested proteins mixtures using a 9.4 Tesla Fourier transform ion cyclotron mass spectrometer", Rapid Comm. Mass Spectrom. 14:1029–1034.

Penn et al., 1997, "Direct analysis of sugar alcohol borate complexes in plant extracts by matrix–assisted laser desorption/ionization fourier transform mass spectrometry", Anal. Chem. 69:2471–2477.

Rowley et al., 2000, "Applications of protein mass spectrometry in cell biology", Methods 20:383–397.

Schnölzer et al., 1996, "Protease–catalyzed incorporation of $^{18}O$ into peptide fragments and its application for protein sequencing by electrospray and matrix–assisted laser desorption/ionization mass spectrometry", Electrophoresis 17:945–953.

Scribner et al., 2000, "Analysis of selected herbicide metabolites in surface and ground water of the United States", Sci. Total. Environ. 248:157–167.

Shevchenko et al., 1997, "Rapid 'de novo' peptide sequencing by a combination of nanoelectrospray, isotopic labeling and a quadrupole/time–of–flight mass spectrometer", Rapid Comm. Mass Spectrom. 11:1015–1024.

Smith et al., 1996, "The role of Fourier transform ion cyclotron resonance mass spectroscopy in biological research—new developments and applications", in: *Mass Spectrometry in the Biological Sciences*, Burlingame and Carr, eds., Humana Press, Totowa, NJ, p. 25–68.

Velculescu et al., 1995, "Serial analysis of gene expression", Science 270:484–487.

Wang and Brown, 1991, "A gene expression screen", Proc. Natl. Acad. Sci. USA 88:11505–11509.

Wodicka et al., 1997, "Genome–wide expression monitoring in *Saccharomyces cerevisiae*", Nature Biotechnology 15:1359–1367.

* cited by examiner

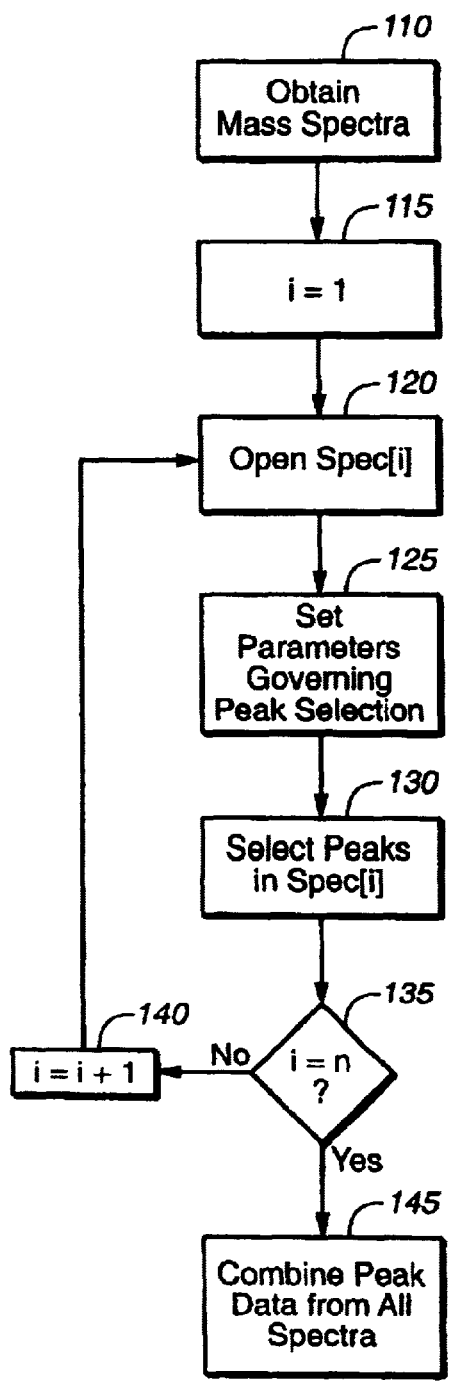
FIG._1
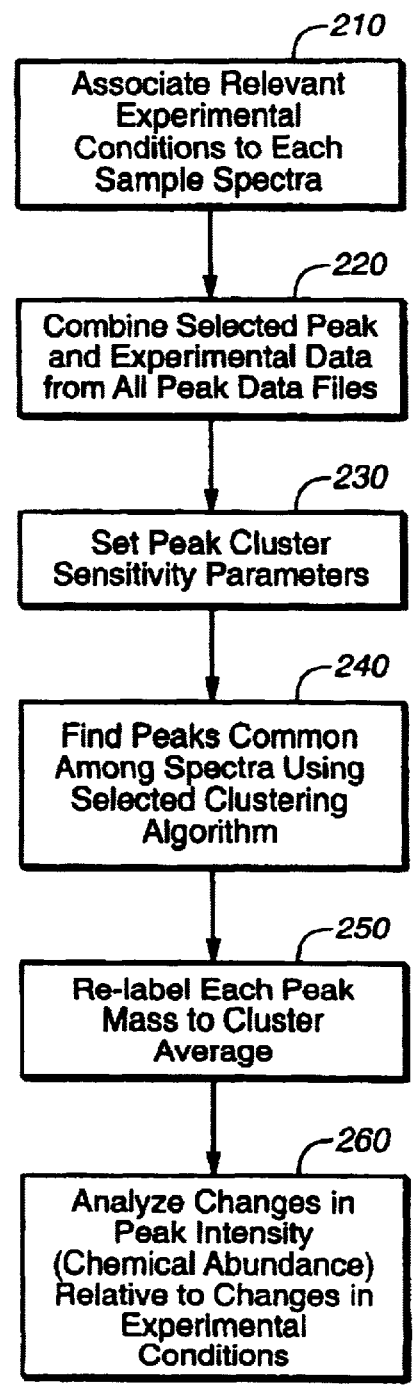
FIG._2

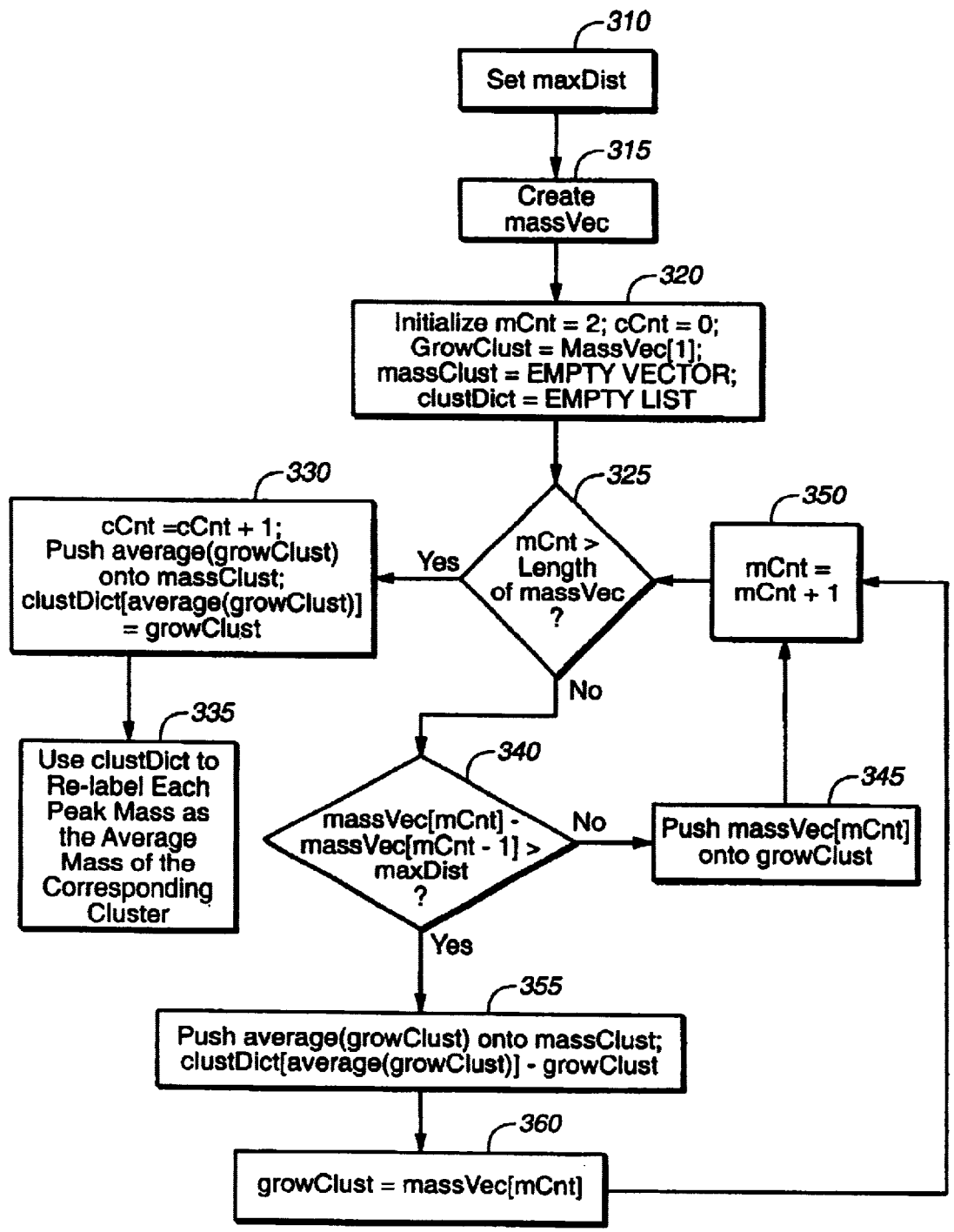
FIG._3

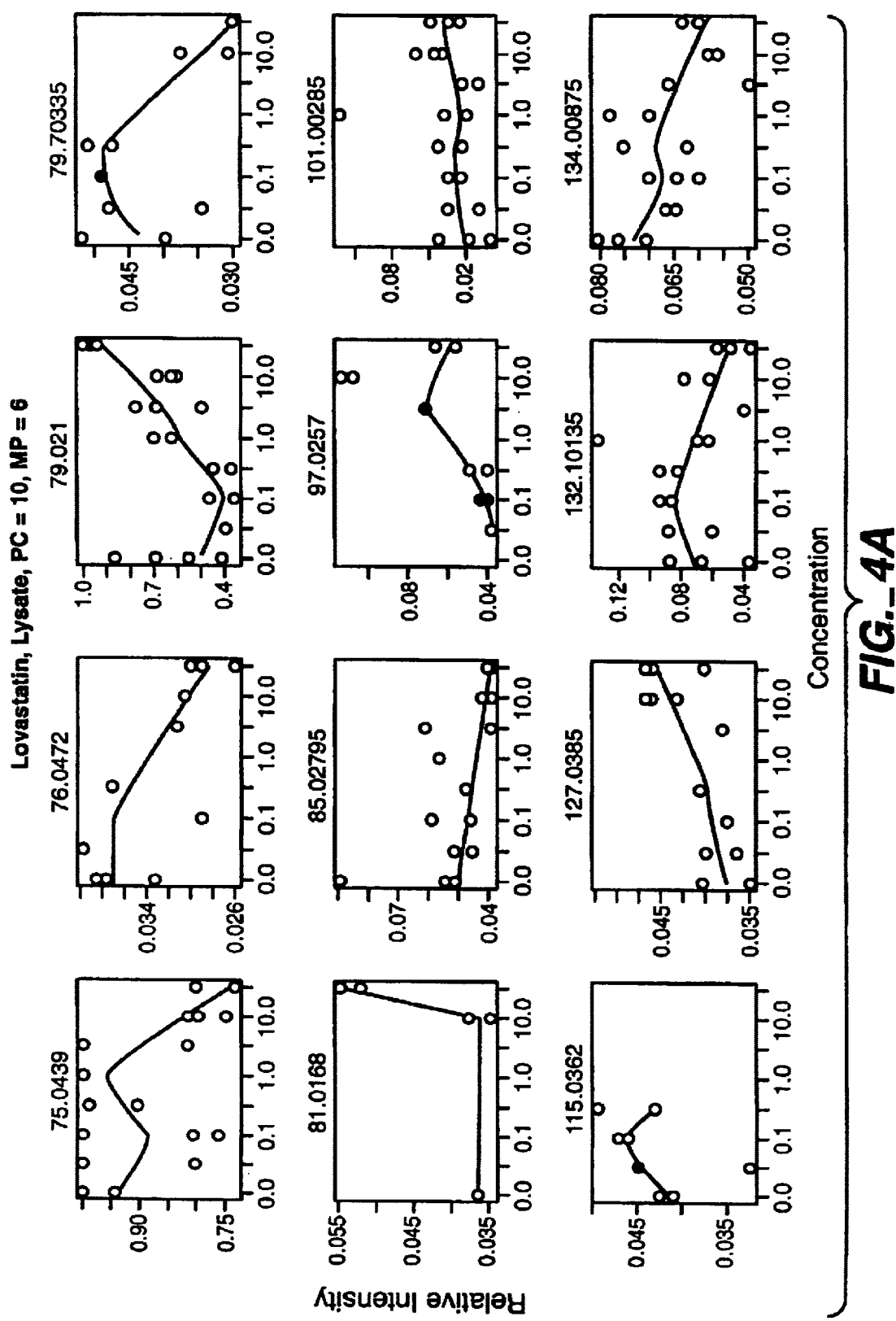
FIG._4A

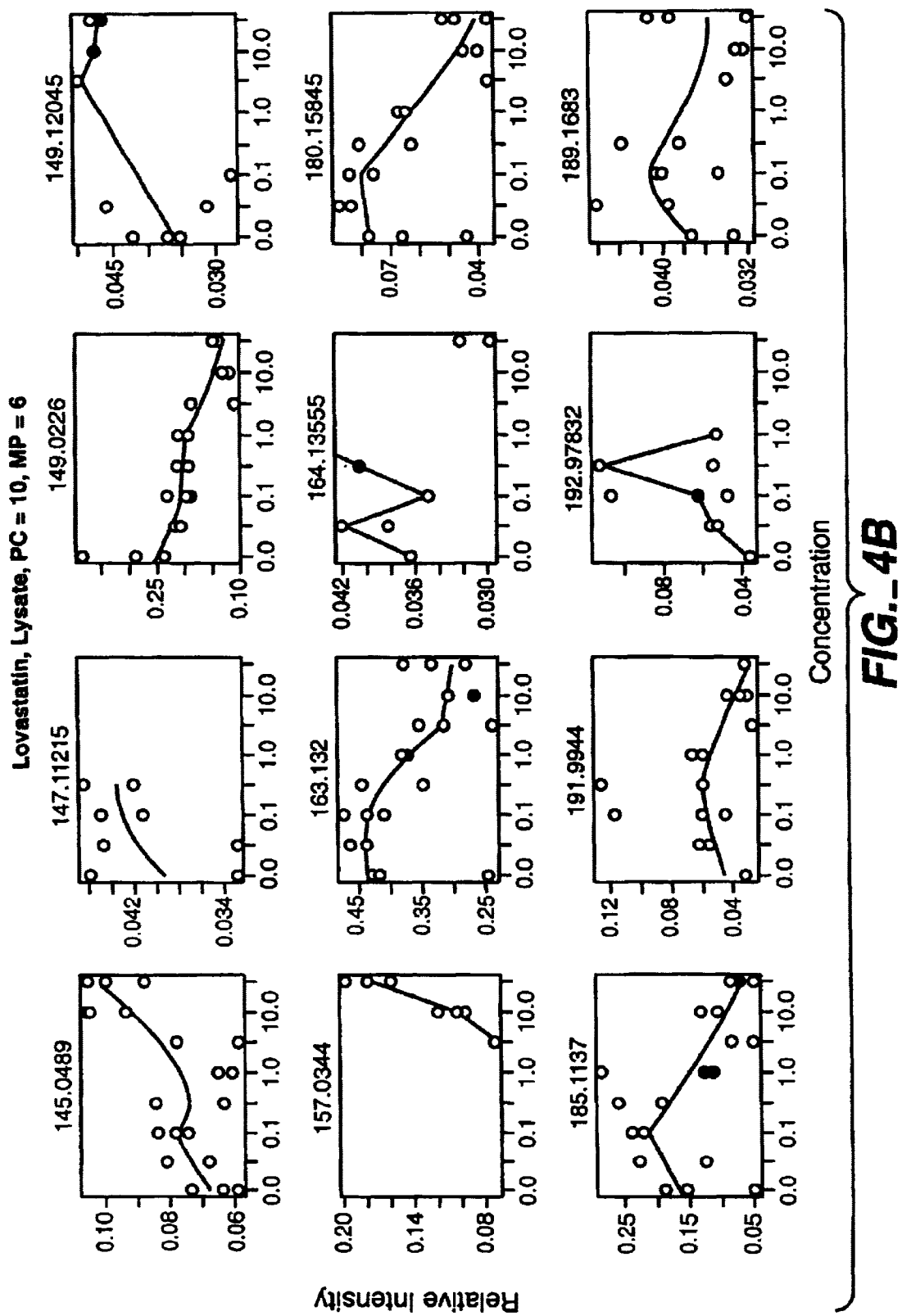
FIG._4B

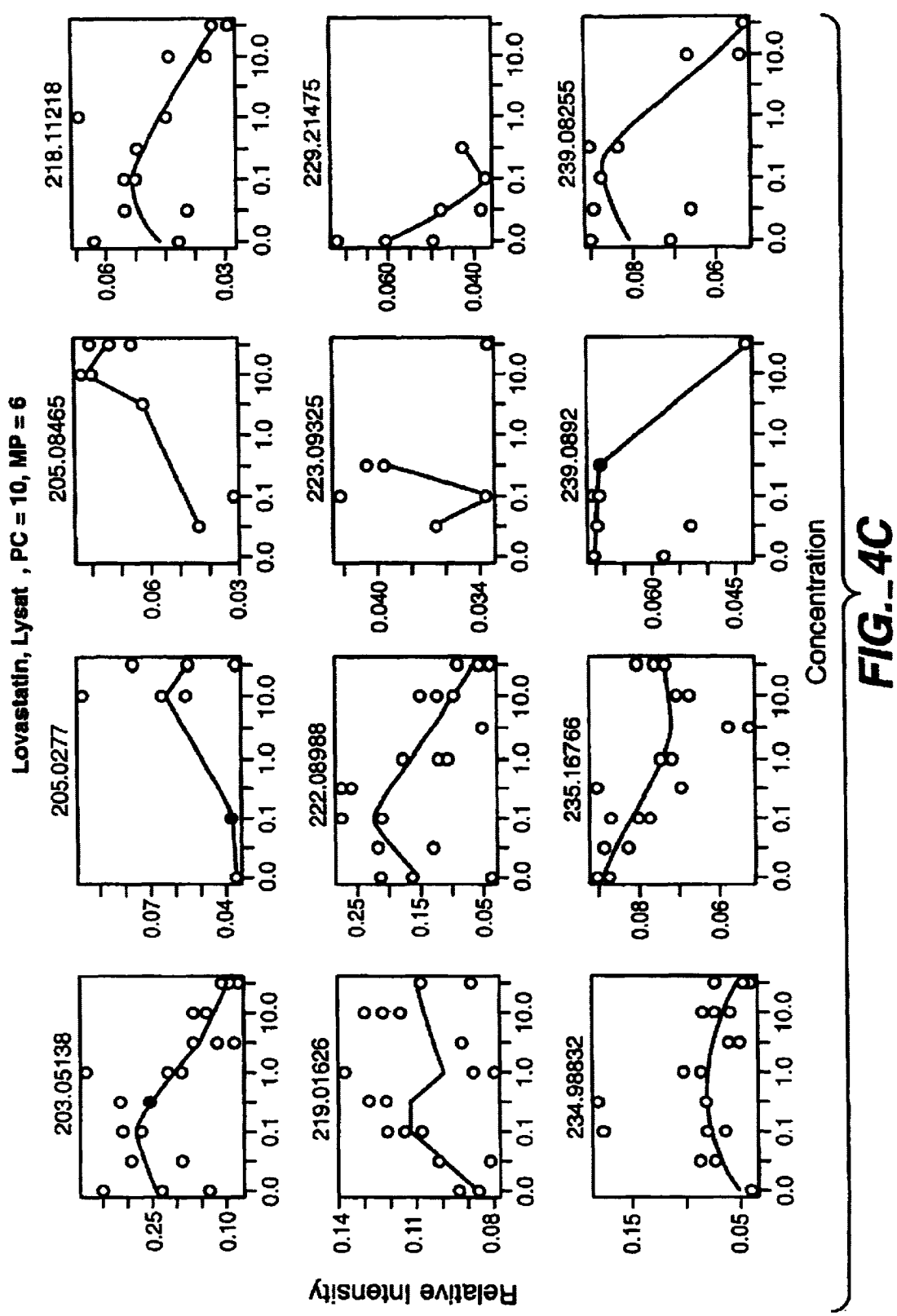
FIG._4C

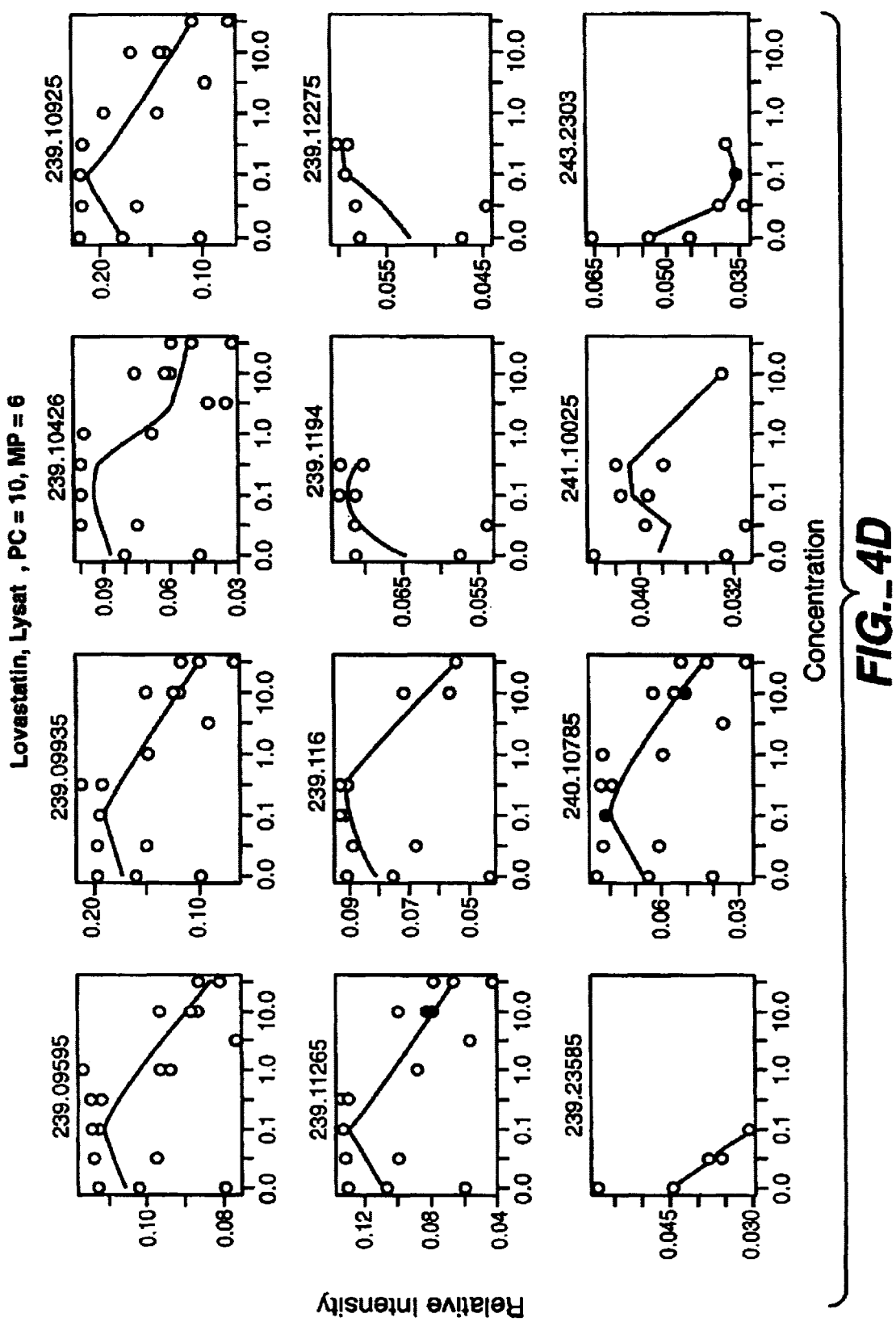
FIG._4D

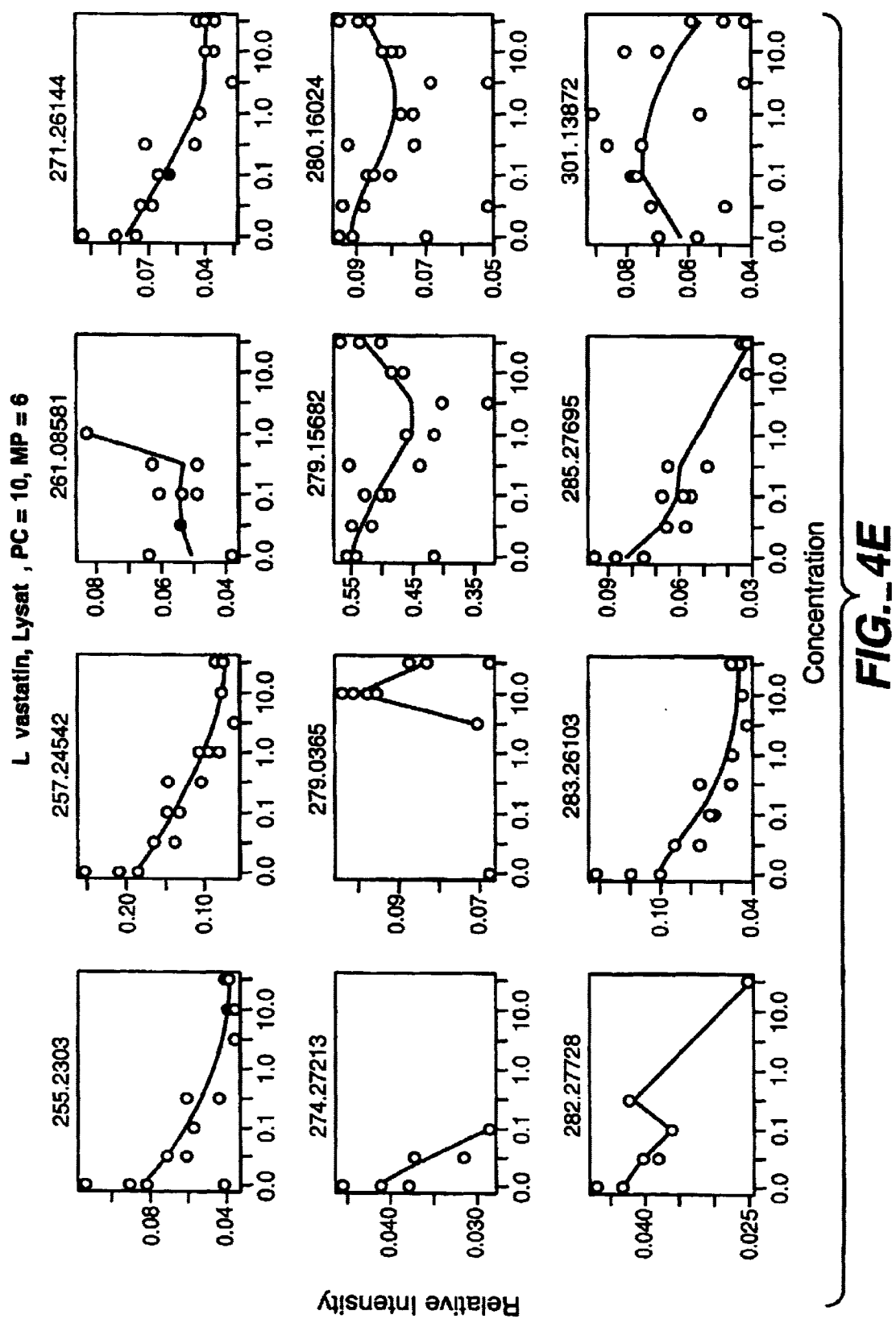
FIG._4E

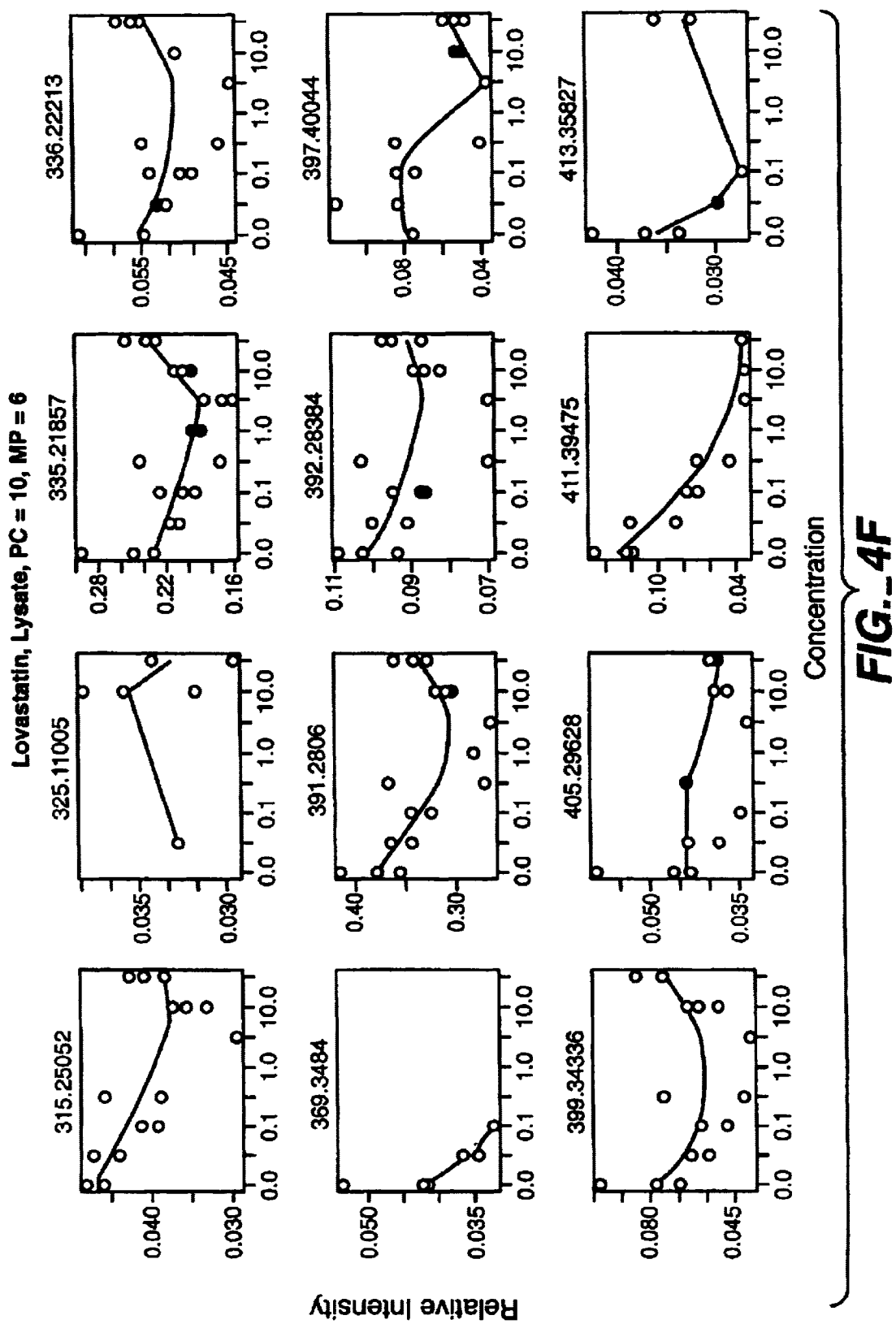
FIG._4F

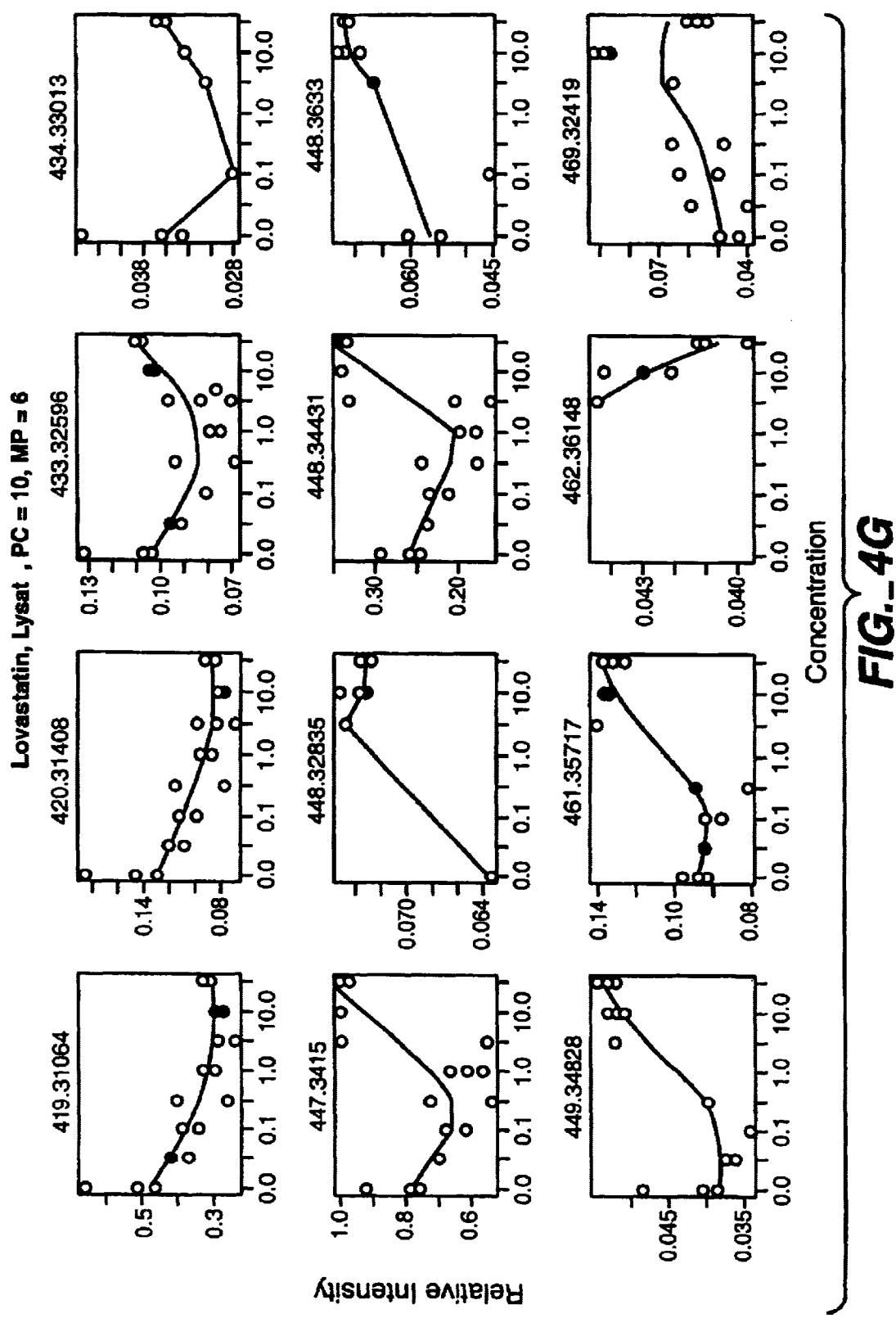
FIG._4G

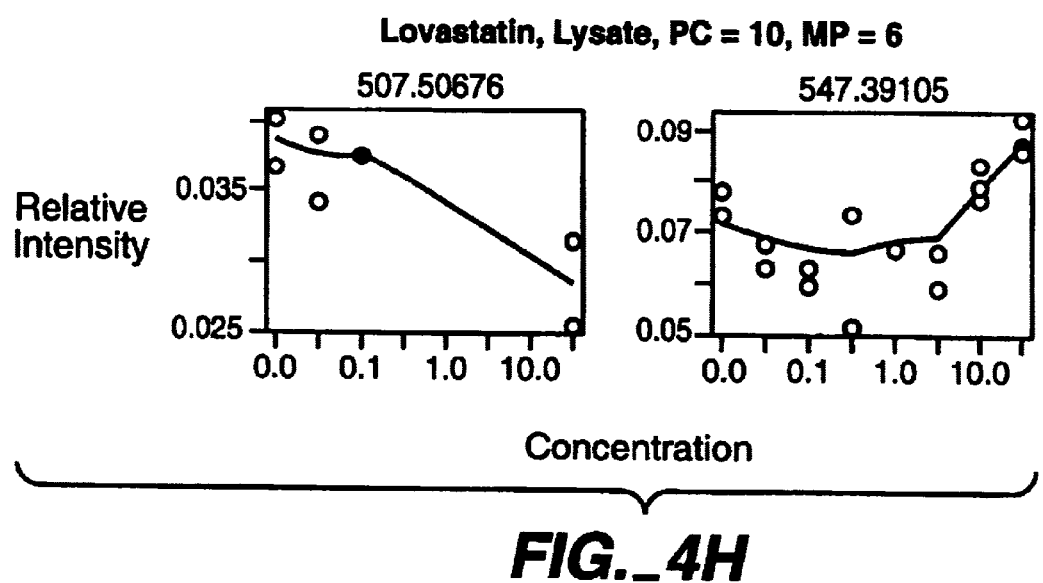
FIG._4H

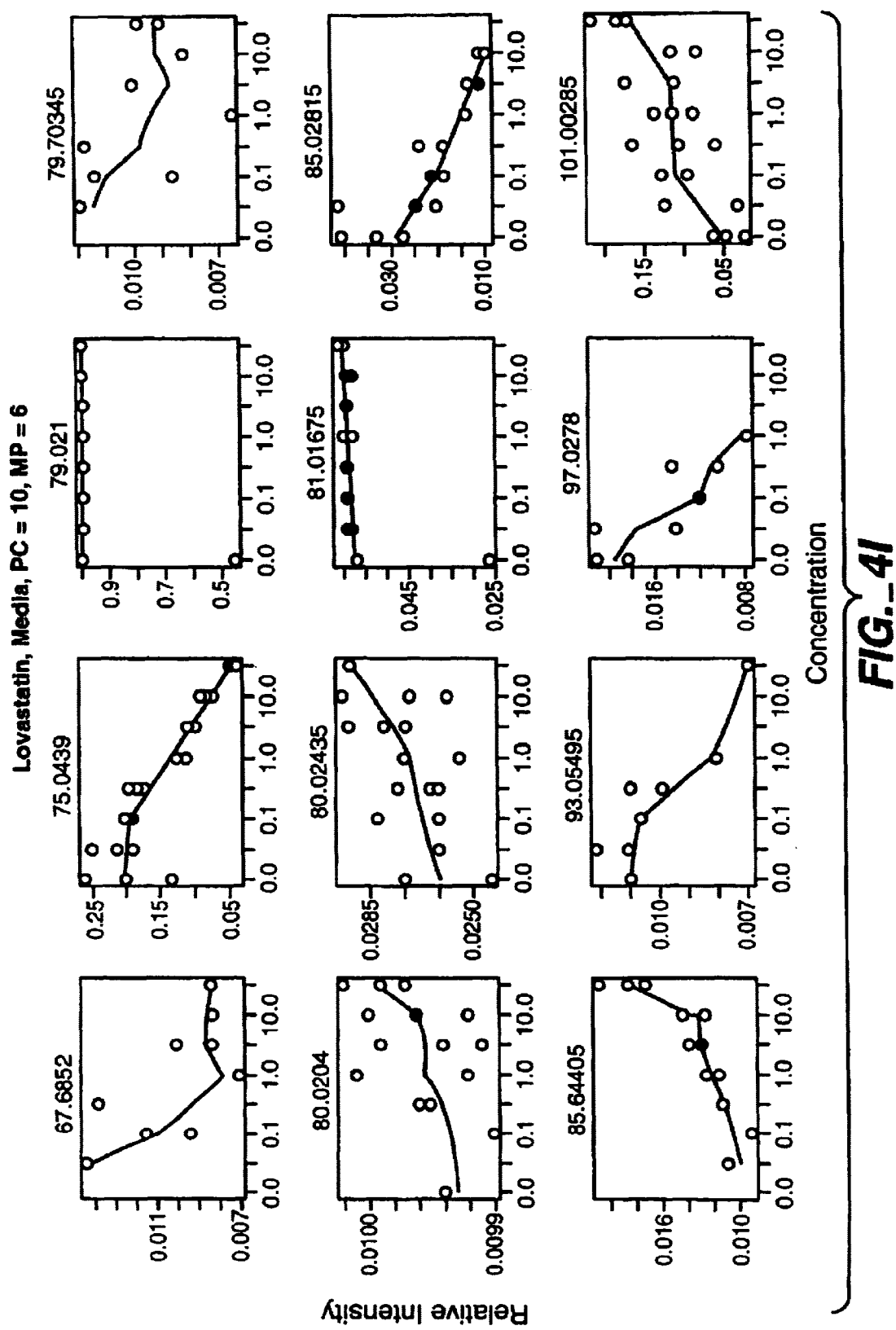
FIG._4I

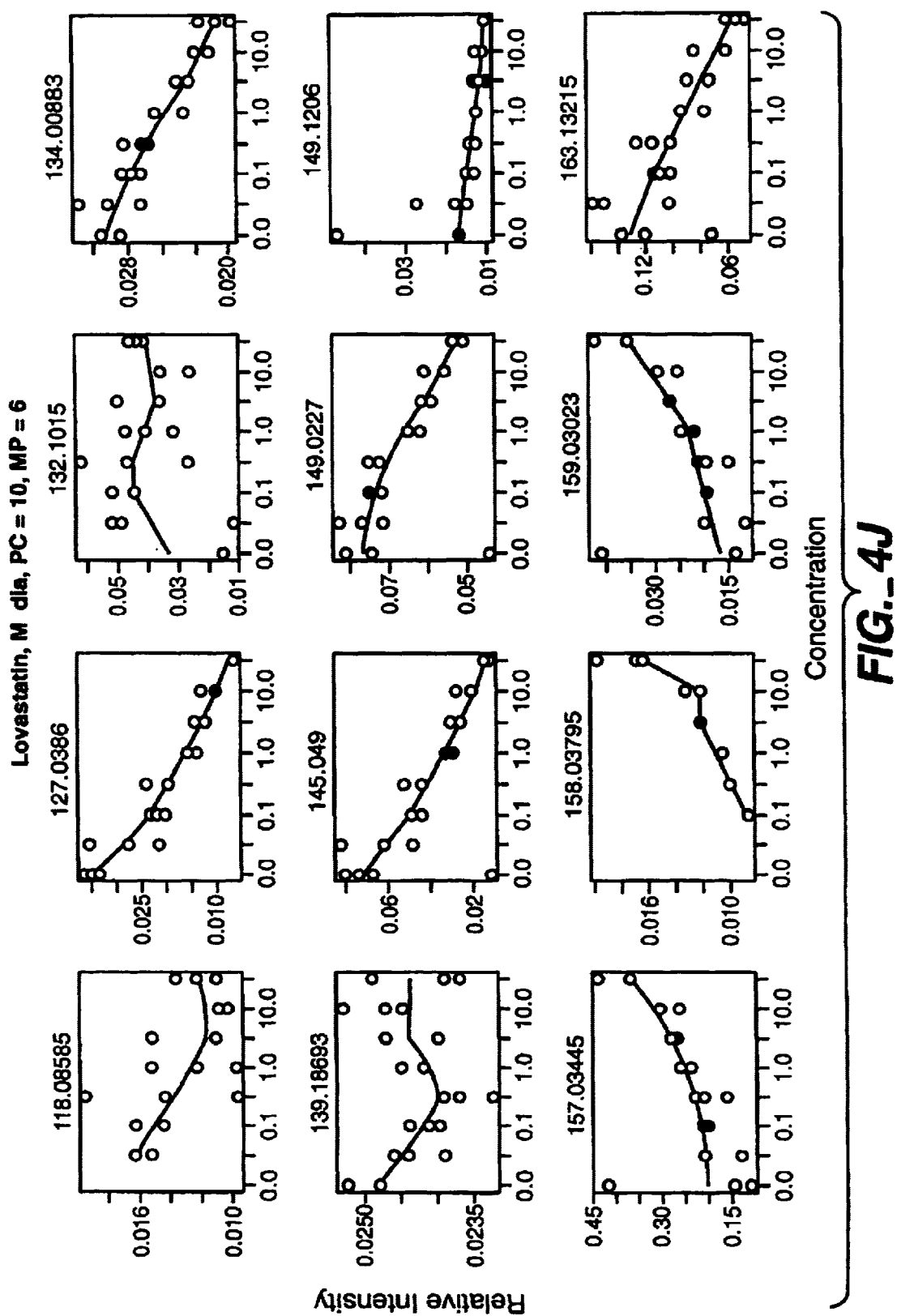
FIG._4J

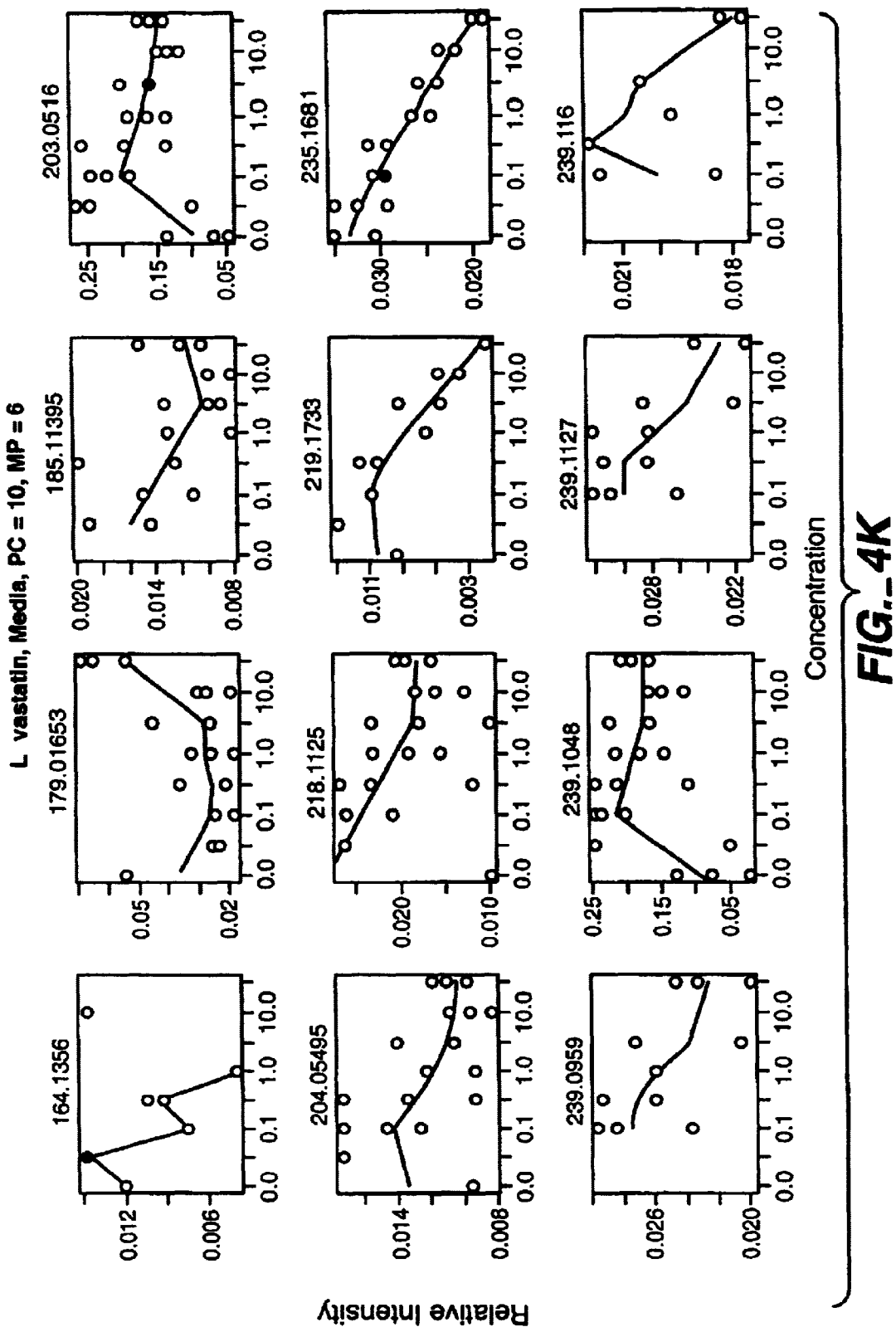
FIG._4K

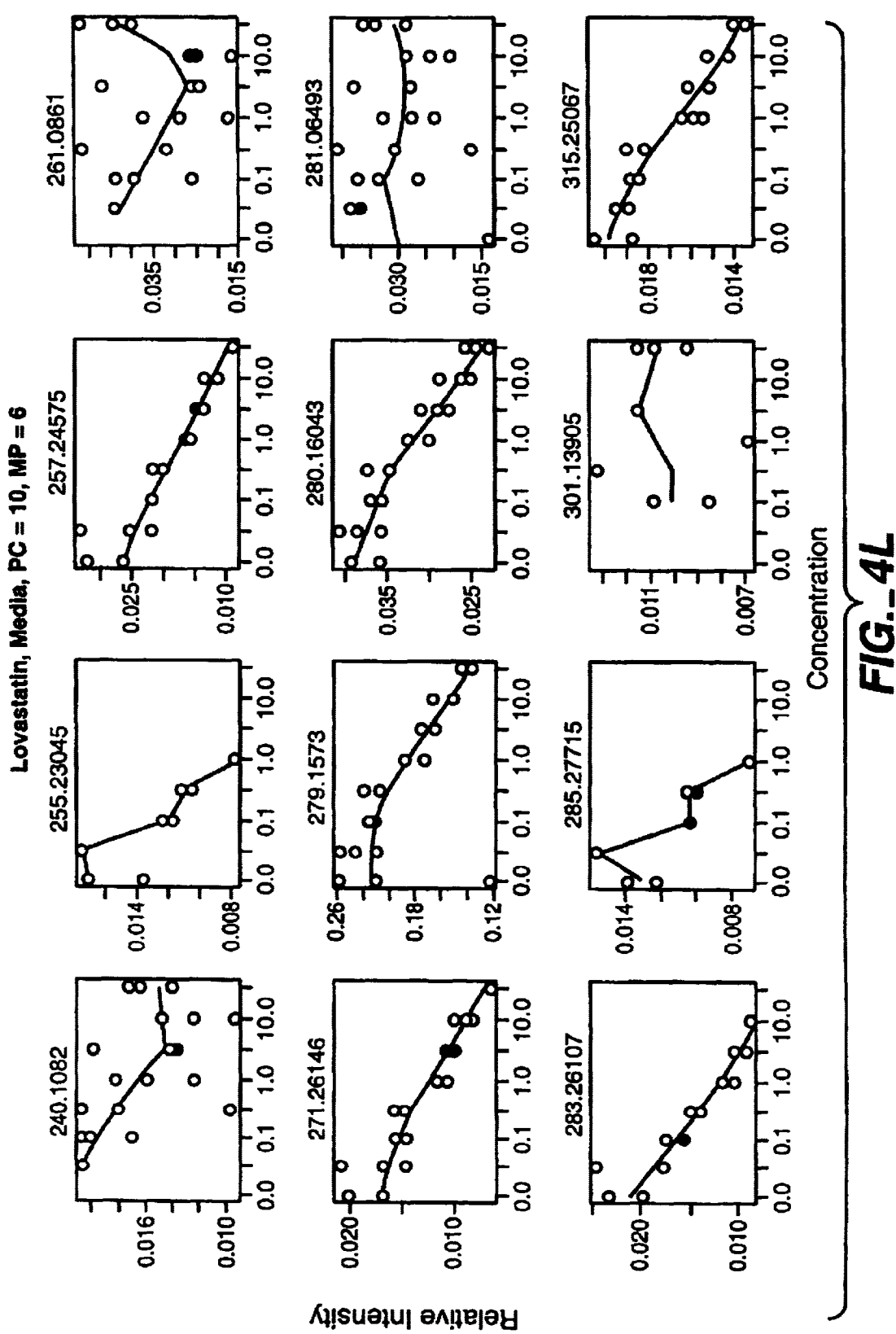
FIG._4L

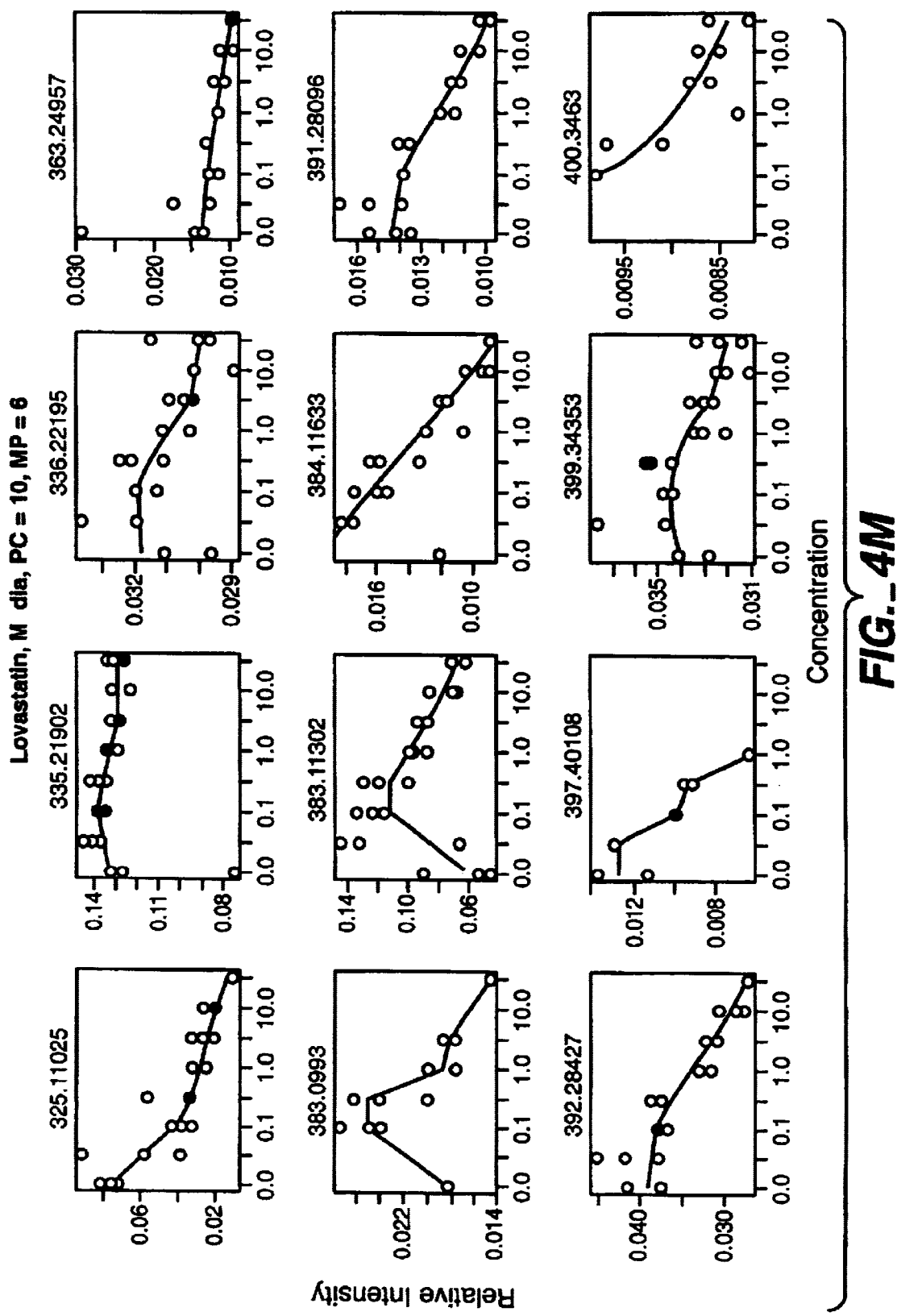
FIG._4M

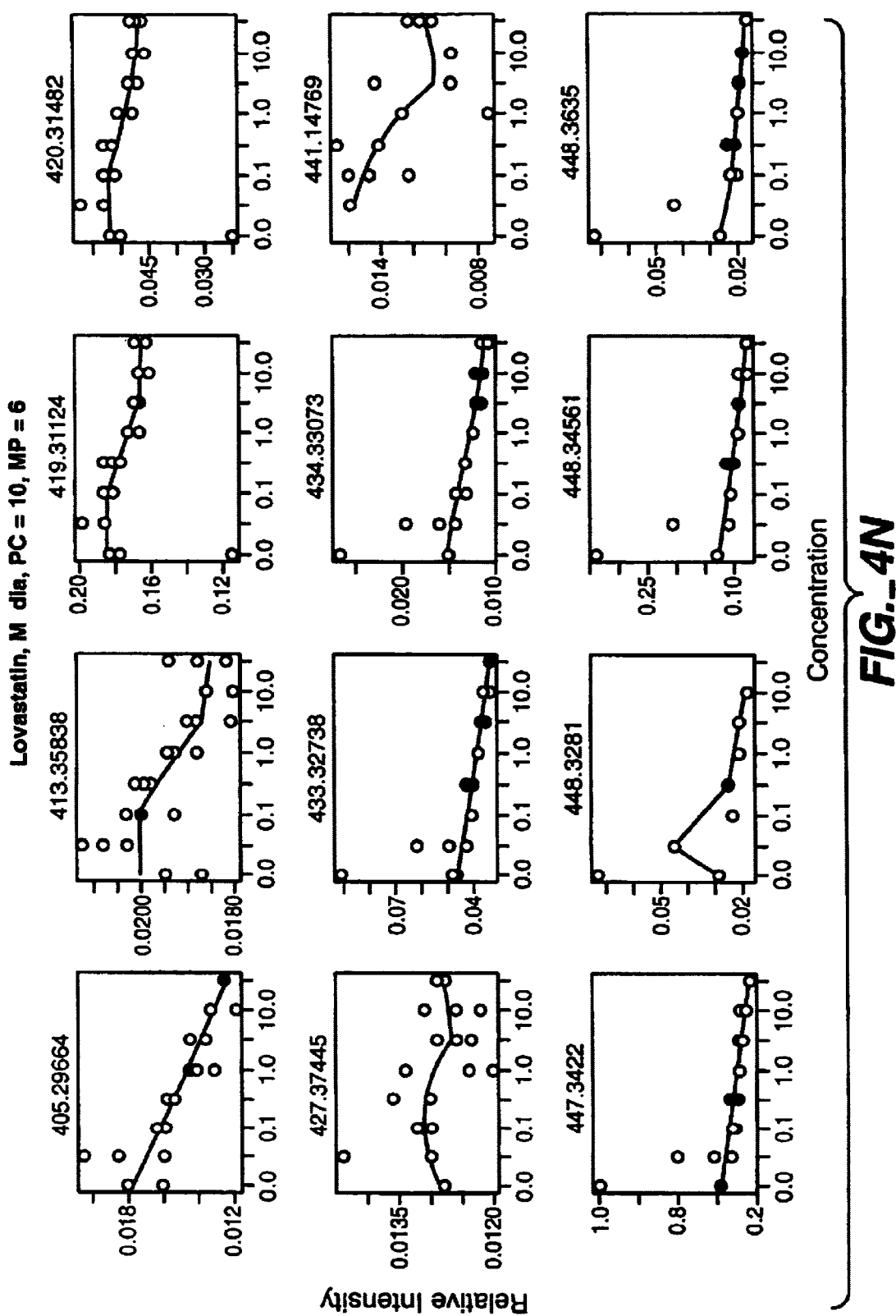
FIG._4N

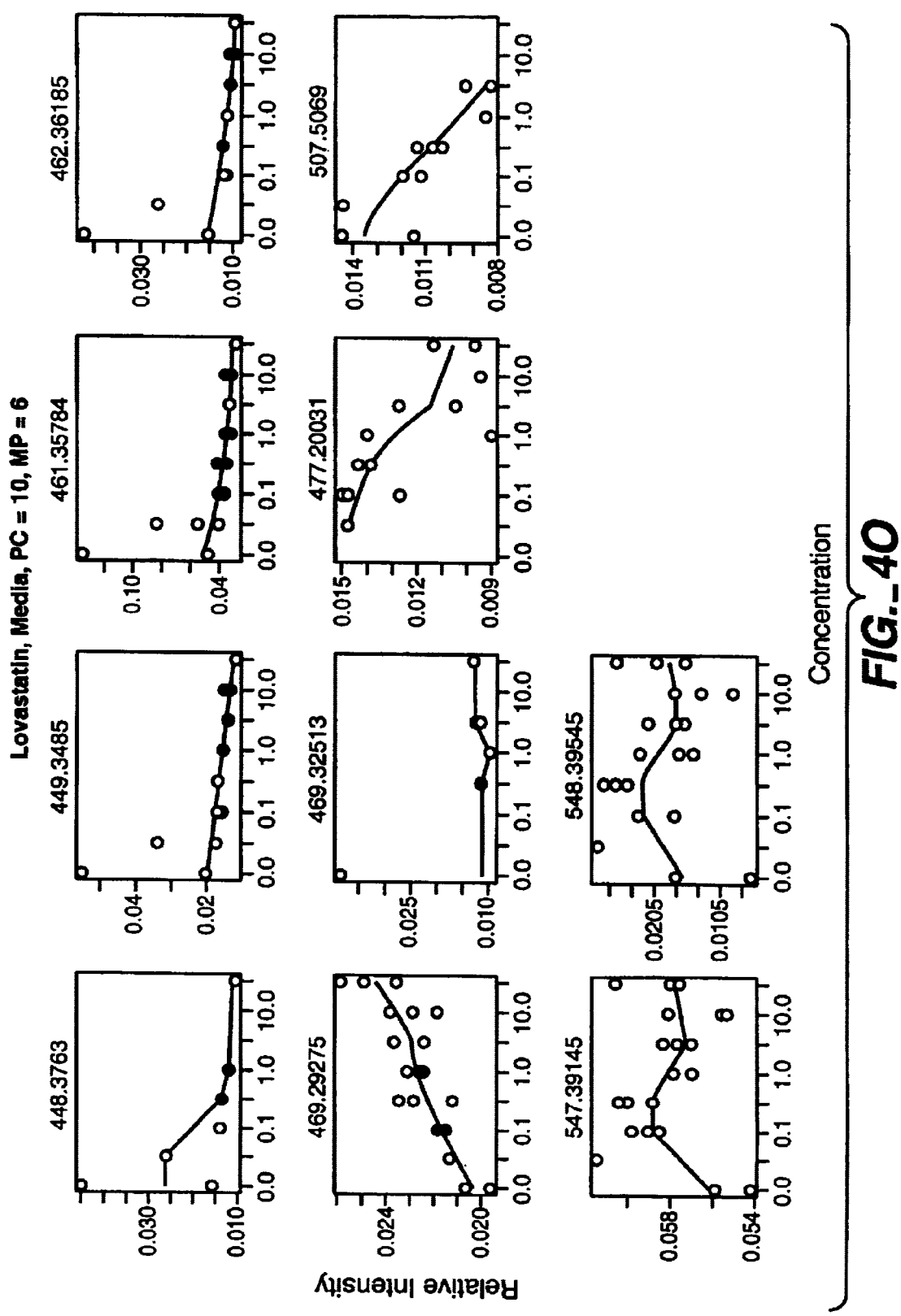
FIG._40

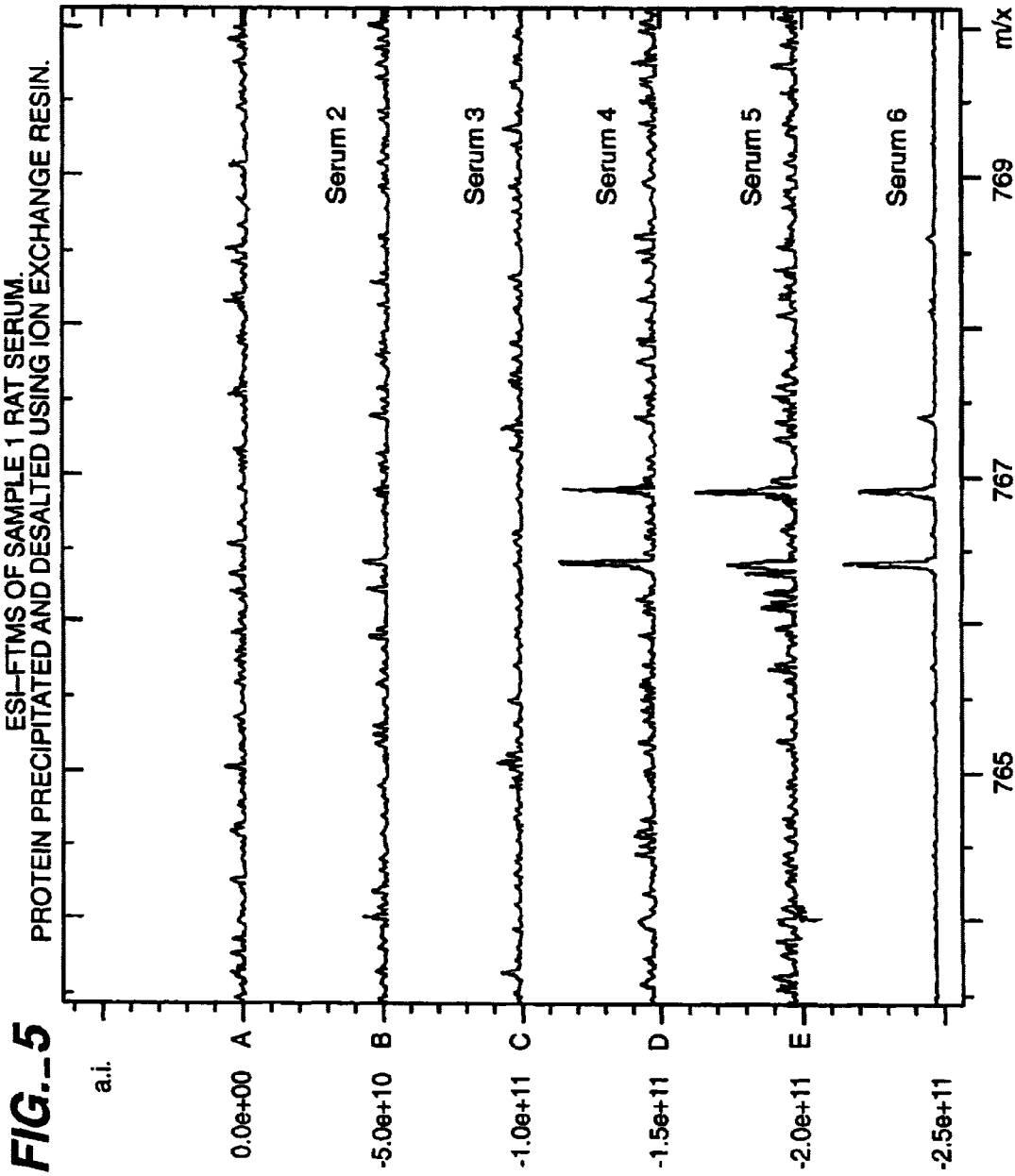
FIG._5

FOURIER TRANSFORM MASS SPECTROMETRY OF COMPLEX BIOLOGICAL SAMPLES

This is a continuing application of U.S. Ser. No. 60/217,663 filed Jul. 10, 2000.

FIELD OF THE INVENTION

The present invention relates to methods for high information content (HIC) analysis or screening of complex biological systems using Fourier transform mass spectrometry (FTMS). The present methods are useful for analyzing complex biological mixtures containing both high molecular weight molecules (e.g., polynucleotides, proteins, polysaccharides) and low molecular weight molecules (e.g., oligonucleotides, peptides, lipids, oligosaccharides, steroid hormones, catabolic and metabolic intermediates) permit the elucidation of molecular differences between complex biological samples, and permit the identification of biologically active molecules (e.g. therapeutically active drugs, etc.).

BACKGROUND OF THE INVENTION

Mass spectrometry is an analytical technique measuring an atom's or a molecule's mass (referred to as atomic and molecular mass, respectively). Since molecular mass is the stoichiometric sum of the atomic masses for each element in the molecule, a characteristic measure is provided for each analyte having a different empirical formula.

The instrument used to measure molecular mass is known as a mass spectrometer. Typically, mass spectrometry is performed by volatilizing (in a gas phase) an analyte then ionizing an analyte and detecting signals. For most types of mass spectrometers, the detector consists of a type of electron multiplier. Ions impinging on such a detector create secondary electrons that register as some measurable current. In this respect, the FTMS instrument is uniquely different in that it measures ions indirectly and non-destructively by measuring an image current. The data generated in fine, i.e., a mass spectrum, has two coordinates: the mass-to-charge ratio scale (x-axis) and the intensity scale (y-axis).

The molecular masses of gas-phase ions, which are formed from both neutral and charged molecules, are determined based on their mass-to-charge (m/z) ratios. If further fragmentation of the gas phase ions is desired, this can be achieved by having them collide with gas molecules, so-called "collision-induced dissociation" (CID). The subfragments that are generated are then also separated by mass.

In recent years, mass spectrometry has been exploited in a variety of biological contexts, including nucleic acid sequencing, peptide sequencing and identification (Keen and Findlay, "Protein Sequencing Techniques," in *Molecular Biology and Biotechnology*, Robert A. Meyers, ed., VCH Publishers, Inc. 1995, p. 771; Carr and Annan, "Overview of Peptide and Protein Analysis by Mass Spectrometry," in *Current Protocols in Molecular Biology*, Ausubel et al., eds., John Wiley & Sons, Inc., 1997, 10.21); detection of in vitro and in vivo protein post-translational modification and expression (Rowley et al., 2000, Methods 20:383–397); elucidation of protein tertiary structure (Last and Robinson, 1999, Curr. Opin. Chem. Biol. 3:564–570); study of labile, non-covalently associated biomolecules (Budnik et al., 2000, Rapid Commun. Mass Spectrom.14:578–584); disease diagnosis (Bartlett and Pourfarzam, 1999, J. Inherit. Metab. Dis. 22:568–571); surveillance of environmental contamination (Scribner et al., 2000, Sci. Total Environ. 248:157–167); agricultural screening (Hau et al., 2000, J. Chromatogr. 878:77–86); and forensic applications (Hollenbeck et al., 1999, J. Forensic Sci. 44:783–788; Gaillard and Pepin, 1999, J. Chromatogr. B. Biomed. Sci. Appl. 733:181–229).

Mass spectrometry, which provides femtomolar sensitivity and accuracy better than 0.01%, has emerged as an attractive alternative to chemical methods for peptide sequencing and identification. Sensitivity of mass spectrometry has been improved by using isotopically labeled peptides and combining a nanoelectrospray ion source with a quadrupole time-of-flight tandem mass spectrometer. This approach exploits an intrinsic feature of the quadrupole time-of-flight device, affording higher sensitivity and resolution than other types of mass spectrometers (Shevchenko et al., 1997, Rapid Comm. Mass Spectrom. 11:1015–1024). Isotopic labeling of C-terminal peptide fragments, e.g., by enzymatic digestion of a protein in 1:1 $^{16}O/^{18}O$ water, provides a characteristic isotopic distribution for these fragments that can be readily identified (Schnolzer et al., 1996, Electrophoresis, 17:945–953); thereby revealing the amino acid sequence.

Mass spectrometry can also be used to study a protein's structure. This technology can provide accurate molecular masses for minute quantities of proteins of interest with masses up to 500,000 Daltons ("Da"). The resulting spectra also can help determine protein folding, protein self-association and other conformational changes and tertiary structure (Nguyen et al., 1995, J Chromatogr A 705:213–45). In addition, co- and post-translational modifications of proteins can be identified and mapped. This method is preferable to using chemical methods such as C-terminal sequencing, which requires relatively harsh sample treatment that can alter or destroy such protein modifications. Post-translational modifications that can be identified using mass spectrometry include phosphorylation, glycosylation, deamidation, isoaspartyl formation, and disulfide-bond formation.

Mass spectrometry has also found important applications in the study of protein-protein interactions. Target proteins can be followed in vivo to document their conformational changes, active site usage, ligand recognition, assembly into multimeric complexes (e.g., holoenzymes), and trafficking among organelles.

Fourier transform mass spectrometry (FTMS) is also known as Fourier transform ion cyclotron resonance (FTICR). The principle of molecular mass determination used in FTMS is based on a linear relationship between an ion's mass and its cyclotron frequency. In an uniform magnetic field, an ion will process about the center of the magnetic field in a periodic, circular motion known as cyclotron motion. An ensemble of ions having a particular mass-to-charge ratio (m/z) can be made to undergo cyclotron motion in-phase, producing an image current. The image current is detected between a pair of receive electrodes, producing a sine-wave signal. The Fourier transform is a mathematical deconvolution method used to separate the signals from many different m/z ensembles into a frequency, also known as mass, spectrum. Unlike other forms of mass spectrometry, FTMS is non-destructive. For a general review of FTMS, see Hendrickson and Emmett, 1999, Ann. Rev. Phys. Chem. 50:517–536. The application of FTMS to biological sciences is generally similar to other mass spectrometry applications. See, e.g., Smith et al., 1996, "The Role of Fourier Transform Ion Cyclotron Resonance Mass Spectrometry in Biological research—New Developments and Applications" in *Mass Spectrometry in the Biological*

Sciences eds. A. L. Burlingame and S. A. Carr, Humana Press, Totowa, N.J.; McLafferty, 1994, Acc. Chem. Res. 27:379–386.

A number of researchers have started evaluating the use of FTMS in the analysis of biological samples; see Jensen et al., Electrophoresis 2000 21:1372–1380; Jensen et al., Anal. Chem. 1999 71:2076–2084; Palblad et al., Rapid Comm. Mass Spec 2000, 14:1029–1034; WO 95/25281; WO 00/29987; WO00/03240; WO99/58727; WO99/57318; WO99/46047; Li et al., Anal. Chem. 1999 71:4397–4402; Penn et al., Anal. Chem. 1997; 669:2471–2477; and U.S. Pat. Nos. 6,017,093 and 4,224,031.

Analytical methods useful in drug discovery are primarily based on individual end-point observations. The targeting of specific biological interactions (e.g., receptor-ligand, substrate-enzyme) for xenobiotic intervention has been a common paradigm for mining chemical libraries. The traditional approach of choice for drug discovery by pharmaceutical, biotechnology and genomics companies is classical high throughput screening (HTS), which entails parallel screening of large chemical libraries on single targets using generally cell-free assays. Chemical libraries used in HTS are most often generated using combinatorial chemistry. Collections of chemicals obtained from natural sources or generated using "conventional" chemistry are used to a lesser extent in HTS.

The HTS approach is premised on validated targets, usually proteins (e.g., enzymes, receptors, transfer proteins) or nucleic acids (genes, mRNAs). Therefore, the target protein or nucleic acid used in screening by HTS generally is known and thought to play a role in the diseased state. Only then are modulators of the target protein sought as lead compounds for drug development. Workers have conducted HTS on targets only to find later that the target protein was irrelevant to the disease. For example, because receptors can exist in the form of different subtypes, only one of which may be critically essential, a knockout mouse targeting the wrong receptor subtype would likely fail to show a relevant phenotype. It is becoming clear that many biological functions are supported by redundant biochemical pathways. When a pathway fails, redundant mechanisms take over. Many drugs developed on the basis of a defined target show little to no therapeutic activity in vivo because redundant biochemical pathways bypass the pathway in which the target is involved.

For HTS to be successful, the targets usually require an appropriate cellular environment or biological context. For example, a membrane receptor should be in a membrane similar to that in which the receptor is normally found; otherwise, the receptor's properties may be artificially affected. A suitable membrane setting may require reconstituting the membrane with the appropriate lipids. Reconstitution of the suitable membrane environment is the most challenging task in such situations, because of a lack of sufficiently detailed knowledge of the components of such an environment, or because of the complexity of the natural membrane setting.

Additionally, successful classical HTS requires knowledge of the mechanism of the disease or disorder of interest, allowing the selection of a suitable target for validation and, eventually, screening. In the absence of such detailed knowledge, classical HTS cannot be performed.

Another limitation of the technique is that HTS based on a validated target uncovers modulators only of that target. Ultimately, the costly and laborious screening procedure can, at best, provide a small subset of potential test compounds.

Therefore, a method that allows unbiased, simultaneous screening for modulators of multiple, unvalidated targets in their natural environments would greatly improve the pace of drug discovery, while reducing costs. In particular, the identification of small molecules that are present in abnormal amounts in specific states (disease states, development states, differentiation states, etc.) should facilitate the design of analogs, agonists or antagonists of these molecules, leading to the rapid identification of high specificity drugs including but not limited to pharmaceutical drugs, drugs for veterinary applications, drugs for agricultural applications (weed killers, parasite/insect killers, phytohormone agonists, etc.) and drugs for environmental uses (bacterial killers, bacterial proliferators for oil spill cleaning, mussel proliferation controllers, algae proliferation controllers, etc.).

"Bioinformatics" generally refers to the management of biological data using computational means, including data storage (registration of data in an effective way to easily retrieve information) and data analysis using computer intensive mathematical calculations (statistical analysis, non-linear analysis, etc.). Bioinformatics is intensely used to determine structure-activity relationships using the large amount of data generated using High Throughput Screening and Combinatorial Chemistry in order to design more effective biologically active molecules. The state of bioinformatics has evolved from needing to organize and make accessible the glut of gene sequence information that has become available in the past two decades. While initially used to catalog normal gene sequences, bioinformatics is expanding to encompass the identification of protein structures based on pattern recognition in primary sequences and gene expression data obtained using microarrays (see, e.g., http://www.ebi.ac.uk).

Methods for gene-expression profiling useful to identify gene products that are differentially expressed or regulated in different cell types (e.g., as a means to identify their function) include differential display, serial analysis of gene expression (SAGE), nucleic acid array technology, subtractive hybridization, proteome analysis, and mass-spectrometry of two-dimensional protein gels. Methods for gene-expression profiling are exemplified by the following references, which describe differential display (Liang and Pardee, 1992, Science 257:967–971), proteome analysis (Humphery-Smith et al., 1997, Electrophoresis 18:1217–1242; Dainese et al., 1997, Electrophoresis 18:432442), SAGE (Velculescu et al., 1995, Science 270:484–487), subtractive hybridization (Wang and Brown, 1991, Proc. Natl. Acad. Sci. U.S.A. 88:11505–11509), and hybridization-based methods of using nucleic acid arrays (Heller et al., 1997, Proc. Natl. Acad. Sci. U.S.A. 94:2150–2155; Lashkari et al., 1997, Proc. Natl. Acad. Sci. U.S.A. 94:13057–13062; Wodicka et al., 1997, Nature Biotechnol. 15:1259–1267).

Genome sequencing projects, such as The Human Genome Project, have created large databases of gene sequences. Biological function, however, cannot be determined solely from nucleotide sequence data, but rather must ultimately be established by studying the gene products at the level of the protein. Only by studying the protein itself can its expression pattern, association with other molecules in vivo, and its role in normal and diseased tissue be recognized. Recognizing these shortcomings of genomics, scientists have adopted the "Proteomics" approach. The field of proteomics has advanced by utilizing two-dimensional polyacrylamide gel electrophoresis (2-D PAGE), which is capable of resolving thousands of proteins according to their charge and mass. The resulting protein patterns are then compared, and attempts are made to assign unique patterns to particular cell types or disease states. However, 2-D PAGE can fail to resolve the large number of proteins present in complex samples, and the technique is time consuming, labor intensive and expensive. In addition, 2-D PAGE may also significantly fail to detect low abundance proteins. 2-D PAGE has a relative low dynamic range, particularly as compared to FTMS.

Citation or discussion of a reference herein shall not be construed as an admission that such is prior art to the present invention.

SUMMARY OF THE INVENTION

In accordance with the objects outlined above, the present invention provides methods comprising comparing a FTMS peak profile of a first biological sample derived from cells that have not been exposed to a candidate bioactive agent to an FTMS peak profile of a second biological sample derived from a cell that has been exposed to the candidate bioactive agent.

In a further aspect, the present invention provides methods comprising contacting a first population of cells with a first candidate bioactive agent and subjecting the first population of cells to FTMS analysis to obtain a first peak profile. The first profile is compared to a reference profile from the first population of cells in the absence of the first agent.

In an additional aspect, the present invention provides methods comprising subjecting a first population of cells to FTMS analysis to obtain a first peak profile comprising a plurality of peaks, wherein at least two peaks correspond to different types of biomolecules.

In a further aspect, the present invention provides methods comprising a population of cells comprising at least a first and a second subpopulation of cells and contacting the first subpopulation of cells with a first candidate bioactive agent. The second subpopulation of cells is contacted with a second candidate bioactive agent and subjected the first and the second subpopulation of cells are subjected to FTMS analysis to obtain a first and a second peak profile, respectively. The first and said second peak profiles are compared to a reference profile from the population of cells in the absence of the agents.

In an additional aspect, the present invention provides methods comprising contacting a first population of cells with a drug and subjecting the population of cells to FTMS analysis to obtain a peak profile. The profile is compared to a reference profile from said population of cells in the absence of said drug.

In a further aspect, the present invention provides methods comprising providing a population of cells comprising at least a first and a second subpopulation and contacting the first subpopulation of cells with a drug at a first concentration and contacting the second subpopulation of cells with a drug at a second concentration. The first and second subpopulations of cells are subjected to FTMS analysis to obtain a first and a second peak profile, respectively. The first and second peak profiles are compared to identify at least one peak that differs in intensity, which peak does not correspond to the drug.

In an additional aspect, the present invention provides methods comprising subjecting a first population of cells to FTMS analysis to obtain a first peak profile and subjecting a second population of cells to FTMS analysis to obtain a second peak profile, wherein said first and second populations are of different cell types. The first and second peak profiles are compared to identify at least one peak that differs in intensity.

In a further aspect, the present invention provides methods to use SAR (software activity relationship) software in combination with FTMS analysis to generate chemical hypotheses and create new biologically active molecules.

In an additional aspect, the present invention provides methods of determining the components and pathways of disease states. The methods comprise subjecting a population of cells from an organism with a disease state to FTMS analysis to obtain a first peak profile. The peak profile is then compared to a reference profile from cells from an organism without the disease state, or to cells from the same organism from a non-disease tissue. The comparison results in the identification of at least one peak that either differs in intensity or is present in one profile but not the other. The cellular component that gives rise to this peak is then identified. This information can be used in a variety of ways. Databases can be searched for the binding partners of the cellular component to elucidate the cellular pathways of the disease state. The cellular component or its binding partners can be used in screens for drug candidates.

In a further aspect, the invention provides screening methods for the discovery of new drugs. The methods comprise the use of any number of prescreening methods comprising adding candidate agents to cells and screening for altered phenotypes. Cells exhibiting altered phenotypes are then subjected to FTMS analysis and relevant peaks identified. Alternatively, once peak profiles of desirable effects are generated, screening for candidate drugs, such as those generated in structure-activity relationship (SAR) studies that mimic these desirable peak profiles can be done.

In an additional aspect, the present invention provides methods for de novo drug design. The methods include generating a plurality of FTMS analyses on a limited set or library of candidate compounds. The resulting peak profiles are then compared to desirable peak profiles (e.g. those that have been generated using known drugs or disease-free cells) to identify "shapes", "pharmacophores" or "active sites" that are relevant. The results can then be screened against virtual chemical libraries to identify additional compounds for testing in traditional and FTMS screening.

BRIEF DESCRIPTION OF THE DRAWINGS

FIG. 1 illustrates steps of a preferred process for selecting peaks.

FIG. 2 illustrates steps of preferred process for analyzing HICS-FTMS results for a biological sample.

FIG. 3 illustrates steps of a preferred process for identifying peaks common among mass spectra.

FIG. 4A–FIG. 4O HICS-FTMS Data Analysis Software was used to analyze 82 low molecular mass peaks of the HICS-FTMS spectra generated from extracts of rat hepatocytes after they had been treated with various concentrations of lovastatin. Plotted on y-axes are the relative intensities of each peak (normalized against the intensities of the peaks from untreated hepatocytes) against the concentration of lovastatin in $\mu M$ on the x-axes. The number at the top of each graph is the molecular mass of the corresponding molecule. LOWESS was used to perform linear and non-linear curve fitting. Logistical regression was used to refine the curve fitting and provide accurate statistical measures.

FIG. 5 provides illustrative spectra of samples derived from the serum of untreated rats (spectra A–C) versus spectra of samples derived from the serum of rats treated daily over the period of one week with 100 mg/kg 6-(6-hydroxy-5,5-dimethylhexyloxy)-2,2-dimethyl-hexan-1-ol) (spectra D–F).

DETAILED DESCRIPTION OF THE INVENTION

The applicants have discovered that FTMS spectra of complex biological samples have the requisite resolution and sensitivity to permit the analysis of individual molecules present in the sample, each of which molecules can give rise to one or more unique FTMS peaks among the peaks in the peak profile of the sample. The ability to home in on specific peaks allows measuring the intensity of the peak, and therefore the relative concentration of the molecule to which the peak corresponds, in the complex biological sample. This feature is particularly useful in comparative studies, and enables the study of a particular molecule in a variety of biological states, and the characterization of each specific biological state, facilitating high information content screening (HICS) or high information content analysis (HICA). High information content screening and analysis by FTMS are hereinafter referred to as HICS-FTMS and HICA-FTMS, respectively. Thus, unlike traditional approaches which investigate, at most, a handful of molecules at a time, HICS-FTMS and HICA-FTMS have more general applicability useful to most biological problems than presently available methods. This encompasses the use of HICS-FTMS and HICA-FTMS to characterize and distinguish biological states at various timepoints in complex systems. In particular, this powerful technique has clinical implications when used to compare normal and diseased states, identify characteristic markers during disease progression, and monitor drug therapies. Moreover, the invention encompasses drug development with the aid of HICS-FTMS by elucidating protein-protein interactions, defining organelle and cytoplasmic constituents, and characterizing multimeric protein complexes.

FTMS provides a number of distinct advantages and benefits over traditional mass spectroscopy (MS). The resolution, accuracy and sensitivity of FTMS make it ideal for the analysis of complex biological samples. These samples may include high-molecular mass components such as nucleic acids, proteins, lipids, and oligosaccharides, including but not limited to lipoproteins, proteoglycans and chemically modified molecules (e.g., phosphorylated proteins), and low molecular mass components, such as peptides, metabolic intermediates, drug metabolites and catabolites. Deciphering the chemical complexity of such a cellular system requires extremely high resolving power and mass accuracy. Of all mass spectrometric techniques, FTMS is most capable of achieving the highest performance in terms of resolving power and mass accuracy.

In addition, the non-destructive nature of FTMS allows for the analysis and re-analysis of small amounts of sample, and the resolution allows for the specific characterization and identification of different cellular components. Thus, one advantage is that while the dynamic mass range of these techniques during any particular run may be on the order of $10^3$ to $10^4$, sequential analysis allows the expansion of this range. FTMS might eliminate the need to have pretreatment separation (2D-PAGE, HPLC, GC, etc.) as required in using classical Mass spectrometry; FTMS has a higher dynamic range than 2D-PAGE. In addition, as the magnet strength of FTMS increases as the technology grows, the dynamic range and resolving power will increase. In addition, the non-destructive quality of FTMS may allow for the analysis of different types of biomolecules (e.g. proteins, lipids, carbohydrates, metabolites, etc.) at once or in sequential runs on the same sample or on similar samples. That is, the non-destructive nature of FTMS allows for the generation of robust information, by varying initial experimental conditions, by varying the preparative steps and by varying solvents and run conditions (including mass cutoffs).

Thus, the present invention provides a number of different assays and analyses to allow the elucidation of a variety of cellular components, mechanisms and pathways. There are three core utilities for the present invention. In a preferred embodiment, the present invention is used to elucidate and discover components and pathways of disease states. For example, the comparison of disease tissue (or, as outlined below, tissues or cells exposed to different treatments such as heat, stress, etc.) with "normal" tissue allows the elucidation of important molecules involved in the disease. Pathways of disease can also be elucidated.

Secondly, the present invention also provides for the discovery/screening of new drug candidates that can be used to treat disease. For example, having identified relevant effects (e.g. the presence or absence of certain molecules; peaks in a disease spectrum or a spectrum of a drug with a desirable or undesirable effect), chemical libraries of drug candidates can be screened for a duplication or avoidance of a relevant effect. Thus, for example, new chemical libraries can be screened for initial "hits", or structure-activity relationships (SAR) can be done once a relevant scaffold has been identified.

Finally, the present invention also provides for de novo drug design as follows. FTMS initial screening of limited libraries of candidate compounds can be done to identify relevant compounds. This can be followed by screening virtual and/or real libraries of pharmacophores to identify structures that may have similar activities. These virtual molecules can then be synthesized and tested for activity.

By comparing FTMS peak profiles from different samples, complex and intensive data can be elucidated; the methods allow the identification of biomolecules that are differentially present in different samples; this includes both changes in the presence or absence of peaks as well as changes in peak intensity. For example, FTMS peak profiles may be obtained from cells that have been exposed to one or more candidate agents or drugs, and compared to profiles from untreated cells to identify cellular changes associated with the drug or compound; for example, toxicity profiles may be obtained or libraries of drug candidates screened for desirable or undesirable effects. Similarly, cells from different disease states, such as cardiovascular disease, cancer, diabetes, obesity, inflammatory diseases, Alzheimer diseases, autoimmune diseases, those infected with pathogens, etc. can be compared to normal tissue profiles to identify the pathways and cellular components affected by the disease. Yet another example involves comparing profiles from different tissues or cell types to identify cell-specific components, to build a database for comparisons with new tissues, disease states, or different individuals.

The methods described herein further permit detection and/or identification of chemical modifications of natural molecules, identification of pathologically induced metabolic pathway modifications, (namely changes in fluxes, accumulation of metabolites, depletion of metabolites, modification of metabolites), identification of iatrogenic effects, identification of biochemical reaction and biochemical pathways, identification of catabolic and metabolic intermediates, identification of redundant biochemical/metabolic pathways, identification of SOS biochemical/metabolic pathways, and the identification of apoptosis pathways. Metabolic intermediates and metabolites of interest include but are not limited to natural metabolites, molecules synthesized or degraded in vivo, molecules modified during oxidation or reduction reactions, in cells and in biological fluids, as well as various small and large molecules that are present in food (e.g., vitamins, foreign substances) or are generated by enzymatic digestion of food (e.g., amino acids, particularly essential amino acids, fatty acids), as well as catabolites and xenobiotics.

In addition, the methods of the invention can be used to generate a number of databases for use in analyzing samples. For example, the methods can be used to generate a database of metabolic transformations occurring in vivo. That is, reference molecules (e.g. scaffolds) containing chemical substructures of interest are administered and new or altered metabolites are identified by FTMS. For example, metabolic transformations of secondary amines or secondary alcohols can be identified, registered and put in an inventory database. Any new compound with a secondary amine will be evaluated using the metabolic transformation database. Similarly, the present invention can be used to generate highly accurate small molecule databases.

Thus, the present invention provides compositions and methods involved in Fourier Transform Mass Spectroscopy (FTMS) analysis. FTMS can be done on any number of samples. As will be appreciated by those in the art, the sample may comprise any number of things, including, but not limited to, cells (including both primary cells and cultured cell lines), tissues and bodily fluids (including, but not limited to, blood, urine, serum, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g. fluid obtained from an abscess or any other site of infection or inflammation) or fluid obtained from a joint (e.g. a normal joint or a joint affected by disease such as rheumatoid arthritis, osteoarthritis, gout or septic arthritis) of virtually any organism, with mammalian samples being preferred and human samples being particularly preferred; environmental samples (including, but not limited to, air, agricultural, water and soil samples); biological warfare agent samples; research samples including extracellullar fluids, extracellular supernatants from cell cultures, inclusion bodies in bacteria, cellular compartments, cellular periplasm, mitochondria compartment, etc., purified samples, extraterrestrial samples such as meteorites, etc. As will be appreciated by those in the art and outlined below, the samples may be either "native", e.g. without further manipulation or treatment, or "treated", which can include any number of treatments, including exposure to candidate agents including drugs, genetic engineering (e.g. the addition or deletion of a gene), etc. This is to be distinguished from the treatment or preparation of the samples for FTMS analysis, as further described below.

In a preferred embodiment, FTMS is done on samples comprising cells. As will be appreciated by those in the art, there are a wide variety of cell types that find use in the present invention, including both eukaryotic and prokaryotic cells, with the former being preferred. Suitable prokaryotic cells include, but are not limited to, bacteria such as *E. coli*, Bacillus species, the extremophile bacteria such as thermophiles, etc., and any or all of the bacteria and organisms listed below, including mycoplasma, rickettsia, planctonic unicellular organisms, Paramecia, Pseudomonas, Nitrosomonas, Nitrobacter etc. Included in this definition are prions and the moieties causing Kreutzfeld-Jacob disease.

Suitable eukaryotic cells include, but are not limited to, insect cells; fungi such as yeast and filamentous fungi, including species of Aspergillus, Trichoderma, Pichia and Neurospora, mycoplasms, etc. and including flowering structures and spores as well as lichens; plant cells including those of algae, corn, sorghum, tobacco, canola, soybean, cotton, tomato, potato, alfalfa, sunflower, etc., and including flower, stem, sap, leaf and pollen cells, etc.; and animal cells, including fish, birds and mammals. Suitable fish cells include, but are not limited to, those from species of salmon, trout, tilapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, and humans, marine mammals including dolphins and whales, primary cells as well as cell lines, such as human cell lines of any tissue or stem cell type, and stem cells, including pluripotent and non-pluripotent stem cells. In addition, the cells can be tumor cells as outlined below, cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference. As will be appreciated by those in the art, the cells may have a number of formats, including the use of frozen samples (cell and tissues), dehydrated, freeze-dried or embalmed tissues, mummified cells and tissues, dead cells and tissues (forensic analysis as well as ethnology), sporulated bacteria, etc. such as erythrocytes, macrophages and activated macrophages, pluripotent cells, differentiated and non-differentiated cells, stem cells, and cells with extrachromosomes or nucleic acid material. It should also be noted that populations of cells includes the actual animals; that is, an animal may be considered a population of cells.

In a preferred embodiment and as further outlined below, the cells used in FTMS analysis are from different tissues, particularly human tissues. Thus for example, the peak profiles from cells from different tissues can be compared, to allow the elucidation of cell-specific markers as well as non-specific or housekeeping function components. In this embodiment, the cells can be either primary cells or cell lines from brain, skin, lung, endothelial, epithelial, adipose, muscle, bone, stomach, colon, spleen, pancreas, kidney, bladder, heart, lymphatic system, blood, liver, etc. In this embodiment, FTMS profiles from different tissues can be compared and used to build a database, as further outlined below. Similarly, the cells can be from the same tissue but from different individuals to build a database to normalize and evaluate cell-specific markers. The cells may be from the same or different individuals, species, subspecies, subgroup in different biotypes, etc.

In some embodiments, primary cells are compared to cell lines of the same tissue, to identify differences between the two. As is known in the art, some cell lines do not show the same profiles and succeptibility to drugs as primary cells. Thus, the present invention can be used to evaluate cellular differences between the two.

In a preferred embodiment, comparisons between different cell states or cells subjected to different treatments can be evaluated using the techniques of the present invention. For example, suitable differential treatments include, but are not limited to, physical treatment (stress, heat, cold, pressure, irradiation, etc.), treatments with growth hormones or metamorphosis hormones (e.g. in caterpillar, amphibians), treatments with chemical excitants (coffee, drugs, excitatory amino acids, etc.) and treatments with electrical excitation (e.g. in nerves, muscle cells).

In a preferred embodiment, the cells are from an animal with a disease state. "Disease state" in this context includes any ailment for which either information, diagnosis or treatment is desired. The disease state may be the result of genetic disease (including genetic diseases based on protein changes such as cystic fibrosis or sickle cell anemia, or the presence of particular single nucleotide polymorphisms, mutations in tumor suppressor genes, etc.), somatic cell changes, etc. Accordingly, suitable disease state cells are those from cancer, cardiovascular disease, viral or bacterial infection, obesity, diabetes, inflammatory disease, autoimmune disease, etc. Similarly, cells from individuals with chromosomal abnormalities (e.g. trisomy, etc.), pre- or post gene therapy, etc.

In a preferred embodiment, cancerous cells or tissues are used in the present invention. In this embodiment, suitable tumor cells include, but are not limited to, those from skin cancers including melanoma, myeloid leukemia, carcinomas of the lung, breast, ovaries, colon, kidney, prostate, pancreas, stomach, brain, lymphatic system, thymus, thyroid, adrenals, testes, etc.

In a preferred embodiment, the cells are obtained from individuals with cardiovascular disease. Thus, suitable disease state cells in this embodiment include, but are not limited to, cardiomyocytes, endothelial cells of the circulatory system, macrophages, liver cells (hepatocytes), adipocytes, smooth muscle cells, intestinal cells, etc.

In a preferred embodiment, the cells are obtained from individuals with diabetes. Thus, suitable disease state cells in this embodiment include, but are not limited to, cardiomyocytes, endothelial cells of the circulatory system, macrophages, pancreas cells, liver cells (hepatocytes), adipocytes, smooth muscle cells, intestinal cells, etc.

In a preferred embodiment, the cells are obtained from individuals with obesity. Thus, suitable disease state cells in this embodiment include, but are not limited to, cardiomyocytes, endothelial cells of the circulatory system, macrophages, liver cells (hepatocytes), adipocytes, smooth muscle cells, intestinal cells, etc.

In a preferred embodiment, the disease state cells are classified as such due to infection with viruses or bacteria. Suitable viruses include, but are not limited to, orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses. Suitable bacteria include, but are not limited to, a wide variety of pathogenic and non-pathogenic prokaryotes of interest including Bacillus; Vibrio, e.g. *V. cholerae*; Escherichia, e.g. Enterotoxigenic *E. coli*, Shigella, e.g. *S. dysenteriae*; Salmonella, e.g. *S. typhi*; Mycobacterium e.g. *M. tuberculosis, M. leprae*; Clostridium, e.g. *C. botulinum, C. tetani, C. difficile,* C.perfringens; Cornyebacterium, e.g. *C. diphtheriae*; Streptococcus, *S. pyogenes, S. pneumoniae*; Staphylococcus, e.g. *S. aureus*; Haemophilus, e.g. *H. influenzae*; Neisseria, e.g. *N. meningitidis, N. gonorrhoeae*; Yersinia, e.g. *G. lamblia, Y. pestis*, mycoplasms, rikettias, Pseudomonas, e.g. *P. aeruginosa, P. putida*; Leischmania, Chlamydia, e.g. *C. trachomatis*; Bordetelia, e.g. *B. pertussis*; and Treponema, e.g. *T. palladium*. However, in some embodiments, disease state does not include bacterial or viral infection.

In one embodiment, the cells may be genetically engineered, that is, contain exogeneous nucleic acid (e.g. "knock-in" cells or transgenic animals) or have nucleic acids (including genes) deleted or altered (e.g. "knock-out" cells or transgenic animals).

In a preferred embodiment as is more fully outlined below, cells from disease states are compared to cells from corresponding tissue that do not have the disease, i.e. normal tissue, to elucidate the differences. The normal sample can be from the same individual or a second individual, including family members, twins, etc. In addition, the normal sample may be from post-treatment, e.g. after receipt of bone marrow transplants, chemotherapy, etc.

In a preferred embodiment, the cells are exposed to one or more candidate bioactive agents (sometimes referred to herein as "drugs" or "biomodulatbrs") prior to FTMS analysis. The term "candidate bioactive agent" or "biomodulator" as used herein describes any natural or synthetic molecule, e.g., protein, small organic molecule, carbohydrates (including polysaccharides), polynucleotide, lipids, etc. to be tested in the systems of the invention, particular to be tested for the ability to elicit a response or perturbation in a cellular system. Examples include drugs, antisense or triple helix nucleic acids, ribozymes, hormones, growth factors, cytokines, ligands, antibodies, pheromones, agonists, antagonists, analogs, channel blockers, toxins, weed killers, odors or any other chemical molecules.

Candidate agents encompass numerous chemical classes, though typically they are organic molecules, preferably small organic compounds having a molecular weight of more than 100 and less than about 2,500 daltons, with molecules preferably ranging from about 100 to about 1000–1500 being preferred. Candidate agents comprise functional groups necessary for structural interaction with proteins, particularly hydrogen bonding, and typically include at least one of an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, lipids, fatty acids, steroids, purines, pyrimidines, derivatives, structural analogs or combinations thereof. Particularly preferred are small molecules, peptides, peptide analogues, lipid analogues and carbohydrates analogues.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. In addition, new libraries or species of candidate agents can be made by feeding precursor molecules (e.g. chemical scaffolds) to microorganisms (including bacteria, yeast, etc.) or other organisms (plants, actinomycetes, fungi, etc.) to generate new chemicals or difficult to artificially synthesize chemicals/molecules.

Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs. Compounds may be racemic mixtures or isomers.

In addition, one or more libraries can be screened simultaneously or sequentially; the libraries may be related (e.g. orthogonal libraries, synthetic libraries of related scaffolds, natural libraries of plant extracts) or unrelated.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures such as peptoids. Thus "amino acid", or "peptide residue", as used herein means both naturally occurring and synthetic amino acids. For example, homo-phenylalanine, citrulline and noreleucine are considered amino acids for the purposes of the invention.

"Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents. Thus for example libraries of helical amphipathic peptides, beta sheet peptides, amphipathic beta sheet peptides, etc., can be made.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English*, 30:423 (1991); Letsinger, et al., *J. Am. Chem. Soc.*, 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorqanic & Medicinal Chem. Left.*, 4:395 (1994); Jeffs, et al., *J. Biomolecular NMR*, 34:17 (1994); Tetrahedron Left., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine, hypoxanthine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an inter-action library, nature provides a hint with the immune response: a diversity of $10^7$–$10^8$ different anti-bodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^3$ different candidate agents are screened, with at least $10^4$ being preferred, at least $10^5$–$10^6$ being especially preferred, and in some cases, depending on the screening techniques, as many as $10^7$, $10^8$ or $10^9$ different candidate agents, are simultaneously analyzed in the subject methods. Preferred methods maximize library size and diversity.

In a preferred embodiment, the candidate agent is a known drug, e.g. a bioactive agent known to have at least one desirable effect. However, as is more fully outlined below, many drugs have side effects or toxicity issues, and the present invention can be used to elucidate the mechanisms of toxicity and for screening of second generation drug analogs that do not have as many or any side effects. For example, peaks of a spectrum may be associated with toxicity as identified through the use of classical markers or dyes, such as viability dyes, or mass tags as is known in the art. In addition, in some embodiments, two or more drugs are added to the sample simultaneously or sequentially, to allow the elucidation of drug interaction mechanisms and complications or to block one biological/metabolic pathway or an enzyme.

As will be appreciated by those in the art, there are a wide variety of possible drugs that can find use in the present invention, depending on the assay and desired characteristics. For example, in cancer applications, suitable cancer drugs include, but are not limited to, antineoplastic drugs, including alkylating agents such as alkyl sulfonates (busulfan, improsulfan, piposulfan); aziridines (benzodepa, carboquone, meturedepa, uredepa); ethylenimines and methylmelamines (altretamine, triethylenemelamine, triethylenephosphoramide, triethylenethiophosphoramide, trimethylolmelamine); nitrogen mustards (chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard); nitrosoureas (carmustine, chlorozotocin, fotemustine, lomustine, nimustine, ranimustine); dacarbazine, mannomustine, mitobranitol, mitolactol; pipobroman; doxorubicin, and cisplatin (including derivatives).

With particular regard to cardiovascular disease, there are a number of suitable drugs to add to cells to elucidate the mechanism of action, characterize the response at the biomolecule level, or identify relevant biomolecules in the pathway of drug action. These include, but are not limited to, statins (cholesterol lowering agents that block cholesterol synthesis by inhibiting HMGCoA reductase that include atovastatin, pravastain, lovastatin, cerivastatin, synvastatin), fibrates (fenofibrate, bezafibrate, gemfibrozil), niacin, nicontinic acid, oestrogens, bile acid binding resins (including cholestyramine and colestipol hydrochloride), ACAT inhibitors, cholesterol intestinal absorption inhibitors, PPAR ligands (alpha, gamma, etc.), and nuclear factor ligands such as RXR, FXR, ROR, etc.

Suitable diabetes drugs include, but are not limited to, biguanides (including but not limited to metformin, phenformin and bufomin); sulfonylureas (including but not limited to tolbutamide, acetohexamide, tolazamide, chloropropamide, glipizide and glyburide); thazolidinedione derivatives (including, but not limited to, ciglitazone, ploglitazone, englitazone, and troglitazone); and others described in Cornicelli, Atherosclerosis 2(2): 43 (1999), hereby incorporated by reference in its entirety.

Suitable hypertension drugs include but are not limited to, beta blockers, ACE inhibitors, diuretics; angiotensin inhibitors such as losartan, etc.

The candidate bioactive agents are combined or added to a cell or population of cells. Suitable cell types for different embodiments are outlined above. The candidate bioactive agent and the cells are combined. As will be appreciated by those in the art, this may be accomplished in any number of ways, including adding the candidate agents to the surface of the cells, to the media containing the cells, or to a surface on which the cells are growing or in contact with; adding the agents into the cells, for example by using vectors that will introduce the agents into the cells (i.e. when the agents are nucleic acids or proteins). As will be appreciated by those in the art, there are a wide variety of delivery methods available, including the use of vesicles and other vehicles such as liposomes, organic solutions, dispersions, suspensions, electroporation, etc.

In general, the candidate agents are added to the cells (either extracellularly or intracellularly, as outlined above) under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.1 and 4 hours will be sufficient, preferably between 0.1 and 1 hours. Excess reagent is generally removed or washed away.

A variety of other reagents may be included in the reactions and assays, outlined below. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for analysis and screening, as necessary. Washing or rinsing the cells will be done as will be appreciated by those in the art at different times, and may include the use of filtration and centrifugation.

In a preferred embodiment, rather than utilize a chemical or biochemical moiety as a candidate agent, perturbators are used. In this context, the term "perturbator" refers to a physical or non-physical parameter or stimulus that elicits a response or perturbation in a biological system (at the cellular, tissue or organismal level). Physical stimuli include but are not limited to environmental conditions (including but not limited to gas, odors, electrocution, irradiation and other physical effects), living organisms (including but not limited to bacteria, virus, yeast, plant or animal parasite) and foreign substances (e.g., a grafted organ or tissue, an implant). Non-physical stimuli include but are not limited to environmental conditions (including but not limited to cold or hot temperatures, pressure), or emotional states (including but not limited to fear, stress, mental challenge, emotional distress, sexual attraction, and pleasure).

Once the cells have been exposed to the candidate agent (s) and allowed to incubate for some period of time, several steps can be taken. In a preferred embodiment, for example when libraries of candidate agents have been added to the cells, the cells may be screened for an altered phenotype to isolate cells exhibiting a desirable phenotype. These isolated cells are then subjected to FTMS to elucidate and characterize the underlying effects on the biomolecular level. That is, a biochemical "fingerprint" of a desirable phenotype may be generated, and used in drug development programs, for example. Alternatively, when the libraries are small, or when single drugs or sets of drugs have been used, every cell population is subjected to FTMS analysis as outlined below to elucidate the "fingerprint" of the drug's effect. Again, as outlined below, this type of analyses can be used to build databases of different tissues, different drugs, etc.

Thus, in a preferred embodiment, after the introduction of libraries of candidate agents to a population of cells, the cells are screened for a changed phenotype. By "altered phenotype" or "changed physiology" or other grammatical equivalents herein is meant that the phenotype of the cell is altered in some way, preferably in some detectable and/or measurable way. It should be noted that both desirable (e.g. in the case of cancer cells, the appearance of differentiation) and undesirable (e.g. dedifferentiation) phenotypes are useful. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, appearance of lipid inclusion, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the bioactive agent can change the phenotype of the cell in some detectable and/or measurable way.

The altered phenotype may be detected in a wide variety of ways, as will be appreciated by those in the art, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells, etc. In some cases, the altered phenotype may be the change in the FTMS spectrum itself; for example, for diseases or other conditions that do not exhibit large phenotypic changes, the elucidation of the change may be done using FTMS.

In a preferred embodiment, once a cell with an altered phenotype is detected, the cell is isolated from the plurality which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluoroscent one; overgrowth against a background of no or slow growth; death of cells and isolation of DNA or other cell vitality indicator dyes, etc.

The isolated cells, e.g. the cells that exhibit a changed phenotype presumably due to the presence of the candidate agent, are then subjected to FTMS analysis as described below.

One distinct advantage of the present invention is the ability of FTMS to analyze single cells or small populations of cells. This is particularly relevant in the cancer area, as heterogeneity of samples can cause ambiguity. Microdissection of tissues and metastases can allow for very small samples, to include single cells, which can then be analyzed using the present methods. In addition, there are a variety of experimental techniques that allow single cell analysis (e.g. fluorescence-activated cell sorting (FACS)) that can be combined with the techniques of the present invention.

In some embodiments, the candidate agents (including drugs) can be added to the cell lysate, rather than to the intact cells. For example, if the drugs are poorly absorbed, the direct addition to cell lysate can result in the facilitation of the effects. In addition, drug stability or metabolism studies are frequently done with cell homogenates.

In addition, it should be noted that the screening protocols used to screen candidate can utilize any number of high throughput screening (HTS) techniques. In a preferred embodiment, the systems of the invention comprise liquid handling components, including components for loading and unloading fluids at each station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well (or higher) loading blocks; cooled reagent racks; microtitler plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems such as Peltier systems are used for stabilizing the temperature of the heat exchangers such as controlled blocks or platforms to provide accurate temperature control of incubating samples from 40° C. to 100° C.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the presence or absence of labels and the assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluroescence resonance energy transfer (FRET), luminescence, quenching, two-photon excitation, and intensity redistribution; CCD cameras to capture and transform data and images into quantifiable formats; a computer workstation; and one or more barcode readers.

These instruments can fit in a sterile laminar flow or fume hood, or are enclosed, self-contained systems, for cell culture growth and transformation in multi-well plates or tubes and for hazardous operations. Similarly, operations can be performed under controlled environments such as inert gas (for example to prevent lipid oxidation). The living cells will be grown under controlled growth conditions, with controls for temperature, humidity, and gas for time series of the live cell assays. Automated transformation of cells and automated colony pickers will facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. As discussed herein, this may be in addition to or in place of the CPU for the FTMS data analysis. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, supercritical fluids and gases (particularly for extraction), samples, washes, assay components, etc. Similarly, when the sample is limited, all components (capillaries, connections, etc.) can be minimized to avoid large dead volumes or dilution effects.

Once the cells are identified, and the optional candidate agents, including drugs, are added, the cells are prepared for FTMS analysis. As will be appreciated by those in the art, this may range from a simple lysis to more elaborate separation technologies, depending on the class of molecules to be evaluated. As will be appreciated by those in the art, different molecules can be classified by a number of different parameters, including the type of molecule (e.g. proteinaceous, lipid, nucleic acid, carbohydrate, metabolites, small molecules, etc.), the size of the molecule (e.g. "small molecule" usually refers to molecules of less than roughly 2500 to 1500 daltons), or on the basis of other characteristics of the molecule (e.g. polar versus nonpolar, charged, metal-ion containing, binding characteristics, etc. For example, suitable molecules for evaluation include metabolites (including catabolites) produced as products of enzymatic reactions or oxidation/reduction reactions. Such metabolites include various small molecules that are present in food (e.g. vitamins, foreign substances, xenobiotics, toxins, oxidized lipids, pesticides, degraded molecules from xenobiotics, etc.), are generated by enzymatic digestion of food (e.g. amino acids, particularly essential amino acids, fatty acids, particularly essential fatty acids, glycolysis intermediates and end-products), are synthesized by the cells (hormones, neurotransmitters, toxins, prostaglandins, etc.) or are otherwise present (partially metabolized drugs, etc.).

In addition, as will be appreciated by those in the art, stable isotopic labeling or depletion can be done as well.

In general, minimal preparation such as extraction of the cells or cell lysate into a solvent suitable for FTMS is done, with the addition of buffers, salts, and other reagents as needed or desired.

In a preferred embodiment, the preparation of samples for FTMS can be achieved by any method known to those of skill in the art. Preferably, sample preparation includes a desalting step to increase the sensitivity and resolution of the FTMS. In addition, as will be appreciated by those in the art, the combination of preparative steps, solvents, purification and separation schemes, will all depend on the class(es) of biomolecules to be evaluated. However, most of the time no preliminary separation is required.

In one embodiment, samples are prepared by a protein precipitation followed by a desalting treatment. A solution of methanol and water (49:49:2, water:methanol:acetic acid v:v:v) is added to each of the samples and the samples are chilled. This precipitates the proteins to the bottom of the tube. Each tube is then centrifuged and the supernatant decanted. For the desalting step, small amount (approximately 100 mg) of DOWEX ion exchange resin is added to each vial and allowed to sit for approximately 10 minutes. The sample is then centrifuged and the supernatant removed. This solution is then introduced to the mass spectrometer.

Any solvent known to those of skill in the art can be used in conjunction with an ion source in the practice of the present invention. Examples of suitable solvents are dimethylsulfoxide, acetonitrile, N,N-dimethyl formamide, propylene carbonate, methylene chloride, nitromethane, nitrobenzene, hexane, methanol and water. The solvent can comprise more than one solvent. In a preferred embodiment, the solvent is a solution of methanol and water (49:49:2, water:methanol:acetic acid v:v:v).

Selection of a suitable solvent will depend on the type of biomolecules whose detection is to be achieved by FTMS. For example, a solution of methanol and water is used as a solvent when the detection of soluble molecules is to be achieved by the FTMS, while hexane can be used when the detection of apolar molecules such as lipids is to be achieved. In one embodiment of the invention, the sample source (e.g., tissues, cells) is extracted in different solvents and each extraction subjected to FTMS, so that a more complete analysis of the molecules present in the sample source can be accomplished.

Samples are optionally purified or separated before beginning the FTMS procedure. Useful separation techniques include but are not limited to HPLC using turbulent flow chromatography, liquid chromatography, reverse phase chromatography, affinity chromatography, supercritical fluid chromatography, gas chromatography (GC), electrophoresis (including but not limited to capillary electrophoresis, polyacrylamide gel electrophoresis, agarose gel electrophoresis), solid phase extraction, and liquid phase extraction, preferably using different solvents (e.g., chloroform/methanol for lipids, water for polar molecules). The capillary of the ion source could be filled with silica beads (derivatized or not) or other material to perform chromatography/separation.

In addition, it should be noted that purification and separation techniques may be simultaneously or sequentially run on samples, in different orders and in different combinations. Thus for example, a simple protein precipitation may be run on a portion of the sample, and then a HPLC step. Similarly, portions of samples (e.g. portions of the cellular populations) may be subjected to different techniques in the elucidation or identification of peaks.

In a preferred embodiment, only one type of biomolecule is evaluated during a particular FTMS run. For example, the purification/separation schemes may be generated such that only proteins of a given mass will be evaluated. Subsequent FTMS runs may utilize different techniques on the same sample, to allow a different subset of biomolecules to be evaluated.

Alternatively, and also preferably, more than one type of biomolecule is evaluated during a single FTMS run. That is, proteins and lipids, proteins and carbohydrates, proteins and small metabolites, etc. can be evaluated simultaneously in the present invention.

As will be appreciated by those in the art, any number of biomolecules can be analyzed using FTMS. The biomolecules can be all of one type (e.g. proteins), or mixtures. Suitable biomolecules in this context are proteins as defined above, nucleic acids, lipids, carbohydrates, and metabolites.

The biological sample is ionized prior to subjecting the sample to mass spectroscopy. Any ionization method that does not damage the molecules present in the biological sample can be used. Such methods are described by Barker, 1999, "Mass Spectrometry," $2^{nd}$ edition, John Wiley & Sons, Ltd., England.

In one embodiment, the biological sample can be ionized by chemical ionization. Chemical ionization uses a reagent ion, generated by bombarding methane with electrons using an electron impact source, to ionize the molecules of the biological sample by a proton or hydride transfer. Alternatively, electron impact, which uses an electron beam to ionize gas-phase atoms or molecules, can be used directly. Usually generated from a tungsten filament, the electron from the beam ionizes the molecules in the biological sample by knocking off an electron from atoms or molecules.

In another embodiment, the biological sample can be ionized by plasma and glow discharge. Plasma and glow discharge entails the use of a hot, partially-ionized gas at low-pressure between two electrodes to excite and ionize atoms.

In another embodiment, fast-atom bombardment of the biological sample using a high-energy beam of neutral atoms (typically Xe or Ar) is employed to ionize the molecules present in the biological sample. The beam of high energy atoms is produced by accelerating ions from an ion source though a charge-exchange cell, the resulting collisions resulting in ionization of the neutral atom.

In yet another embodiment, field ionization is employed to ionize the molecules present in the biological sample. Electric fields that are sufficiently high to cause molecules to lose electrons are used in field ionization. Such fields can be created in an ion source by applying a high voltage between a cathode and an anode called a field emitter. A field emitter consists of a wire covered with microscopic carbon dendrites, which greatly amplify the effective field at the carbon points.

In yet another embodiment, plasma-desorption ionization is employed to ionize the molecules present in the biological sample. Plasma-desorption ionization exploits the decay of $^{252}$Cf, which produces two fission fragments that travel in opposite directions. One fragment strikes the biological sample knocking out ions from the molecules in the sample, and the other strikes a detector and triggers the start of data acquisition.

In yet another embodiment, the molecules present in the biological sample are ionized by laser ionization. Briefly, a laser pulse ablates material from the surface of a sample, and creates a microplasma that ionizes some of the sample constituents. The laser pulse accomplishes both vaporization and ionization of the sample.

In a preferred embodiment, the molecules present in the biological sample are ionized using matrix-assisted laser desorption ionization (MALDI). The biological sample is dispersed in a solid matrix such as nicotinic acid and a UV laser pulse ablates the matrix. The matrix carries along with it into the gas phase some of the large molecules in an ionized form, after which they can be extracted into a mass spectrometer.

In a most preferred embodiment, electrospray ionization (ESI) is employed to ionize the molecules present in the biological sample. The ESI source consists of a very fine needle and a series of skimmers. A sample solution is sprayed into the source chamber to form droplets. The droplets carry charge when they exit the capillary and, as the solvent evaporates, the droplets disappear leaving highly charged molecules in the biological sample. ESI is preferred because is useful for large biological molecules that are difficult to vaporize or ionize. In addition, nanospray techniques and devices are known in the art and find use in the present invention.

Other ionization methods known to those of skill in the art can be used in the practice of the invention. Such methods include but are not limited to resonance ionization, secondary ionization, and a spark source.

For each ion source described above, positive or negative ionization modes can be employed. In positive ionization mode, a trace of formic acid is often added to aid protonation of the sample molecules; in negative iodination mode a trace of ammonia solution or a volatile amine is added to aid deprotonation of the sample molecules. Proteins and peptides are usually analyzed under positive ionization conditions and saccharides and oligonucleotides under negative ionization conditions.

The samples are then introduced into the FTMS. Fourier transform mass spectrometry (FTMS) is also known as Fourier transform ion cyclotron resonance (FTICR). The principle of molecular mass determination from this technique is based on an inverse linear relationship between an ion's mass and its cyclotron frequency. An ion (or charged particle) subjected to a strong magnetic field experiences a natural circular mode of motion referred to as cyclotron gyration; ions of opposite charge gyrate in opposite directions. In FTMS, cyclotron gyration radially confines the ions; the addition of an electric field perpendicular to the axis of the magnetic field axially confines the ions. This configuration comprises what is commonly referred to as a "trapped-ion" cell. The frequency of the cyclotron gyration of an ion is inversely proportional to its mass-to-charge ratio (m/z) and directly proportional to the strength of the applied magnetic field. Thus, low m/z ions have cyclotron frequencies higher than those of high m/z ions.

When ions having of m/z's are present in the trapped-ion cell, the ion ensemble is excited to larger cyclotron orbits by applying a swept radio frequency excitation. The swept radio frequency excitation contains frequency components corresponding to the cyclotron frequency range of interest. The orbiting ion clouds—ions at each m/z orbit at a unique cyclotron frequency—induce an image current on two or more of the spectrometer's detection electrodes. The image current produces sine waves having the cyclotron frequency of each excited ion cloud. This signal is a superposition sine waves which, when subject to Fourier transform, yields an extremely precise measurement of the cyclotron frequencies of each constituent of the ion ensemble. In particular, this non-destructive image current detection scheme is unique to FTMS and provides a distinctive advantage in sensitivity and versatility compared to conventional destructive detection methods. This non-destructive FTMS detection scheme can be exploited for ion re-measurement, yielding improvements in sensitivity from multiple measurements of the same ion population. The signal-to-noise ratio increases inversely to the square root of the number of measurements; for example, after four measurements the signal-to-noise ratio improves twofold. Another way to increase the signal is to "pump" enough ions in the cell in order to increase the signal. Once the cell is "full", the analysis is performed. MSn where n>2, e.g., tandem or extended multi-stage mass spectrometry studies, can also be performed on an ion population in which fragment ions of interest can be selectively retained in the FTMS cell, further dissociated, and detected again. These multi-stage studies provide increased structural information with a significant improvement in overall sensitivity. FTMS is capable of providing a fentomolar sensitivity of detection.

When performing ion fragmentation, the experience of a mass spectroscopist plays an important role. Molecules corresponding to peaks of low intensity could be fragmented, but all fragments may not be identified because the intensity will be too small. If there are too many fragments, some may be "extinguished" by others.

HICS-FTMS applies FTMS to analyze extremely complex biological mixtures that may provide up to several hundred peaks within a relatively narrow mass range. Unexpectedly, FTMS can provide high resolution which is needed to distinguish a complex mixture's components that may be closely spaced in terms of m/z. FTMS provides higher resolution by providing more distinguishable "channels" for mass. Most biological molecules corresponding to peaks observed in this type of analysis are not identifiable, at least initially, until databases of HICS-FTMS peak profiles and the identities of molecules corresponding to those individual peaks are compiled. The high mass-measurement accuracy attainable with FTMS can be exploited to identify the chemical structures and/or sequences. FTMS is capable of routinely providing mass-measurement errors that are less than (±)–3 ppm and, therefore, resolving extremely small mass differences. For example, $C_{13}H_{20}N_2O_3$ and $C_{14}H_{24}N_2O_2$ have the same nominal mass (MW=252.1468 and 252.1832, respectively), yet are resolvable by using FTMS by virtue of the 0.0364 Da (or 144 ppm relative error) difference in their actual masses.

Any commercially available Fourier transform mass spectrometer can be used in HIC screening and/or analysis. In one embodiment, the mass spectrometer is Ultima FT Mass Spectrometer (which is supplied with a combination of ESI and MALDI ionization systems and is available with 4.7, 7.0, or 9.4T magnets; IonSpec Corporation, Irvine, Calif.). In another embodiment, the mass spectrometer used to practice the present invention is FT/MS® 1000, 2000; FT/MS 2001; T30 FT/MS, T70 FT/MS or NewStar (Finnigan San Jose, Calif.). In a preferred embodiment, the mass spectrometer is APEX III (Bruker Daltonics, Inc.;

Billerica, Mass.), available with a 9.4T magnet and ESI and MALDI sources.

The FTMS can be conducted at an FTMS service lab such as the National High Magnetic Field Lab in Tallahassee, Fla.; the Environmental Molecular Sciences Laboratory (EMSL; Department of Energy, Pacific Northwest National Laboratory (PNNL), Richland, Wash.) provides a publicly available FTMS facility (with an 11.5T wide-bore high performance Fourier transform mass spectrometer and a 7T ESI Fourier transform mass spectrometer).

The magnetic field capability of the mass spectrometer is critical for achieving the resolution required for HIC analysis and screening by FTMS. Preferably, a magnet of at least 7 Tesla (for an upper mass limit of detection of approximately 66 kDa) is be used. Even more preferably, a 9.4 Tesla magnet is be used (for an upper mass limit of detection of approximately 120 kDa).

The biological samples of the invention can be introduced into the mass spectrometer manually (e.g., using a hand operated pipette or syringe) or robotically. For large-scale screening by HICS-FTMS, robotic loading is preferred for improved efficiency.

In one exemplary embodiment, the biological samples are introduced to the mass spectrometer via a 64 $\mu$i.d. PEEK tube that is connected to a autosampling robot (GILSON, model 215). The autosampling robot can be programmed to collect small volumes (30 $\mu$l) from as many as 960 sample wells. If each sample is prepared as a 100 $\mu$l extract, 70 $\mu$l can be saved for future use. Between each injection to the transfer line, the needle and injector are washed with 500 $\mu$l of solution to avoid is cross contamination. A constant flow rate of a mobile phase (30 $\mu$l/min consisting of 49:49:2, methanol, water, acetic acid v:v) is delivered to the ESI source. Aliquots of samples retrieved by the autosampler are loop injected into this stream. Under these conditions, a sampling rate of approximately 1 sample per 3 minutes can be achieved. Once the spectra for the 960 samples are collected and stored digitally, another 960 samples can be introduced into the mass spectrometer. The robot can be programmed for multiple runs.

In addition, a variety of programs can be used to maximize and exploit current techniques. For example, loading of small, reproducible amounts of samples can be accomplished using a variety of microfluidic techniques including capillary electrophoresis techniques that load samples using capillary junctions, forming "T"s. This can result in split samples, wherein a portion is injected into the FTMS and a portion is either stored or used for other analyses; for example, biological assays may be run on a portion of the sample. In addition, the flow rates can be adjusted; for example, when an interesting peak is eluted off the HPLC column, the flow rate may be decreased, for example to allow subsequent fragmentation.

Optionally, as outlined above, the mass spectrometer is coupled to an HPLC robot for sample separation prior to introduction into the mass spectrometer. Standard calibration of the system is additionally done.

As with any high throughput method capable of collecting a large body of information rapidly, data management is an important issue. With the invention described herein, the major types of information will be related to FTMS profiles in different cell types (treated with a test molecule vs. untreated; diseased vs. normal; different tissues; different patient samples; cells of different states of differentiation or stress, etc.), and indirectly, the molecules that differ between the different cell types, and therefore, the effect of a given drug or disease state on the molecule.

As will be appreciated by those in the art, there are a wide variety of methods and systems that can be used to gather and process the information.

The acquisition and basic analysis of HICS-FTMS or HICA-FTMS spectra can exploit the readily available commercial software designed the analysis of complex data. In one embodiment, Omega Version 7, 32-bit Windows 98 software is used for the acquisition and analysis of Fourier transform mass spectra (IonSpec Corporation, Irvine, Calif.). In another embodiment, MassSpec Calculator™ Professional (ChemSW, Fairfield, Calif.) is software optimized for 32-bit processors (Windows 95, 98 or NT) is employed. MassSpec Calculator™ Professional provides drawing, fragmentation, autofragmentation capabilities. The software supports 79 elements, including all elemental data such mass, number of isotopes, and each isotope's mass and relative abundance. In yet another embodiment, software such as XMASS™ or HYSTAR™ used in the acquisition and analysis of Fourier transform mass spectra (Bruker Daltonics, Inc.; Billerica, Mass.). In another embodiment, Charisma Software is employed (Finnigan San Jose, Calif.).

The data obtained using the basic software may be conveniently handled using standard relational or spreadsheet data formats. In addition, in many cases it will be useful to search with each newly obtained molecular sequence against local databases, for example against structures identified through non-public experiments, and eventually against global databases.

Specialized tools can be envisioned to visualize the data that are obtained from the present methods in order to interpret the patterns of gene and protein expression and the spectrum of biological, including metabolic, effects that particular treatments or disease states produce in specific cell or organism types. For example, such tools may involve multiple pairwise comparisons, or an averaging or summation method that depicts the cumulative results of several experiments, for example in order to identify those HICS-FTMS peaks either most frequently altered by treatment with a particular class of drugs, or most frequently associated with a specific side effect as a byproduct of different therapies. Many databases, analysis packages, search engines, and graphical interfaces can be adapted for HICS-FTMS or specially designed for these purposes. Thus, baseline adjustment, signal/peak recognition programs, peak summing programs, a large number of statistical analysis programs including the calculation of average or mean peaks, mass spectrum averaging, standard deviations, hypothesis testing, confidence intervals, clustering analysis, etc. A wide variety of statistical analyses are generally described in texts such as Freund and Walpole, Mathematical Statistics, Prentice Hall, Inc. New Jersey, 1980, hereby incorporated by reference in its entirety.

An exemplary, preferred method for identifying cellular components whose levels change in different cell type comprises the following steps:

1. Select peaks that satisfy given criteria from each of the spectra of interest and write that peak information out to files. (see FIG. 1)
2. Extract the peaks from the various spectra data directories, associate necessary treatment and experimental conditions, and combine data into a single file. Match up peaks among spectra using clustering algorithms and re-label each peak with the average of the masses from the corresponding cluster. (see FIGS. 2 and 3)
3. Analyze the resulting data (treatment conditions, cluster average mass, and relative intensity) for influence of varying treatments on relative intensity (abundance) for each mass cluster (chemical entity).

Peak Selection: Referring to FIG. 1, at step 110 mass spectra are acquired from an Apex II mass spectrometer and processed. A macro written for XMASS software (Version 5.0.10, Bruker Daltonics, Inc.) uses an XMASS internal macro facility to open a predetermined set of mass spectra, one at a time (see steps 115, 135, and 140), at step 120. "Spec[i]" denotes the ith spectrum among all spectra.

At step 125 parameters that regulate the sensitivity (PC), number (MaxPks), and range (pp) for selecting peaks are set. PC is the peak picking sensitivity, related to the acceptable signal-to-noise ratio. Higher values (>=10) of PC select only the high, stand-out peaks from a spectrum. Lower values of PC (<=2.5) pick up greater numbers of peaks that are less well distinguished from the background, allowing the selection of low abundance peaks along with noise. A preferred embodiment uses values of 2.5, 5, and 10. These values were selected based on empirical observations. MaxPks is the maximum number of peaks that will be selected. If MaxPks= 1, then only one (usually the most distinguished) peak will be selected, regardless of the setting of the other parameters. In a preferred embodiment, this value is set to a very high number (e.g., 10,000) such that all peaks satisfying the other parameter constraints will be selected. pp is the function called to actually pick the peaks. When this is called, the range of the spectrum that should be considered is supplied as x and y coordinates. Since all of the peaks in the observed spectra were below 1000 m/z and no peaks were greater than 1.5, in a preferred embodiment these values are set to be: x0=0, y0=0, x1=1000, and y1=2.0.

At step 130 the XMASS peak picking algorithm (pp) to the spectrum is used to select peaks based on the parameters set in step 125. The resulting peaks are written out to an ASCII text file (writePeaks). The data in these files include the mass at each selected peak, and the relative intensity at which it was measured.

Combination of Peak Data from all Spectra: Referring to FIG. 2, at step 210 peaks from each spectrum are stored by XMASS as a separate file in a subdirectory with the corresponding spectrum.

A brief explanation of how the XMASS software organizes spectra is in order. The organization is based entirely on directory hierarchies. A directory is selected where data should be stored as samples are processed. As the samples are processed, they are numbered from one to the total number of samples, and each sample result (spectrum and supporting information) is placed into a subdirectory named for the sample number (XMASS refers to this as an experiment number). Within these experiment number directories, there is a subdirectory called pdata, which has subdirectories numbered, starting with 1, for each time the sample is analyzed (each has its own spectrum). It is within this directory that the ASCII peak files are written. Because the XMASS software has no convenient way of tracking experimental conditions, careful notes must be taken during the processing of samples to relate the generated experiment numbers to these conditions.

At step 220 the data from these files are extracted and combined into a single file together with the relevant information about the treatment and experimental conditions associated with the measured sample that each spectrum represents. A preferred embodiment of the subject invention comprises a program (shown below) in the Perl programming language (Perl, Version 5.0.6, Copyright 1987–2000, Larry Wall) that maps experimental conditions to experiment numbers, opens each peak file, reads the contents of that file and writes out the experimental conditions along with the mass and relative intensity data to a file. All samples of interest should be done at one time so the data can be written into a common file. This process is repeated each time the peaks are re-processed with different values for the sensitivity parameters.

Perl program:

description: This script parses a set of XMASS peak files, adds supporting information regarding sample treatment conditions and joins them together in a single comma delimited data file.

```
@expdir=("t:\\Mass_Spec_Data\\ESP24223_PART1\\",
    "t:\\Mass_Spec_Data\\ESP24223_PART2");
$outfile=
    ("h:\\chemistry\\mass\\data\\peakfiles.esp24223.pc10.csv");
open(OUTFILE, ">$outfile");
@mass=( );
@ri=( );
%comps={ };
for $i (1 . . . 50){
    $comps{$i}="ESP24223"; #All samples treated with
        same compound}
@conc=(0, 0.03, 0.1, 0.3, 1.0, 3, 10, 30); #Compound
    concentrations
%conc={ };
%type={ }; #Sample type
for $i (1 . . . 24){
    $conc{$i}=$conc[int(($i-1)/3)];
    $type{$i}="lysate";
}
for $i (25 . . . 48){
    $conc{$i}=$conc[int(($i-25)/3)];
    $type{$i}="media";
}
print OUTFILE "expno,cmpd,conc,type,mass,r.i.\n";
    #Data file header for $i (1 . . . 48){
    if($i<=17) {
        $infile=$expdir[0]. $i. "\\pdata\\1\\peaks";
    }
    else {
        $infile=$expdir[1]. ($i-17). "\\pdata\\1\\peaks";
    }
    print $infile . "\n";
    $fileline=0;
    open(INFILE, "<$infile");
    while(<INFILE>){
        $fileline+=1;
        if($fileline>2 && /^\s/) {
            @tmp=split(/\s+/, $_);
            if($i<=17) {
                print OUTFILE "esp24223.1.". $i. ",".
                    $comps{$i}.
                    ",".$conc{$i}. ",". $type{$i};
            }
            else{
                print OUTFILE "esp24233.2.". ($i-17) ",".
                    $comps{$i}.
                    ",".$conc{$i}.",".$type{$i};
            }
            # Now add the data
            print OUTFILE ",".$tmp[2].",".$tmp[3]. "\n";
        }
```

}
    close(INFILE);
}
close(OUTFILE);

The data from this combined file is then imported into a statistical programming environment (R, Version 1.01, Ihaka & Gentleman (1996), "R: A Language for Data Analysis and Graphics", Journal of Computational and Graphical Statistics 5:299–314).

It is very common for there to be small variations in the reported peak masses representing the same chemical entity among spectra. Therefore, to allow for meaningful comparison of peaks among spectra, peaks that likely correspond to the same chemical entity must be identified and appropriately labeled. This task is accomplished using a clustering algorithm.

Referring again to FIG. 2, at step 130 peak cluster sensitivity parameters are set. Peak cluster sensitivity parameters, regardless of the clustering algorithm used, are preferably selected based on practical experience with the data. The goal is to combine all masses across spectra that are believed to represent that same chemical entity, and not any others. At step 140, peaks common among spectra are found using a clustering algorithm. For the clustering process of this step (further illustrated in FIG. 3) and the data at hand from multiple experiments, a maxDist value of 0.0008 has been found to perform remarkably well. Adjoining peaks are rarely mixed and peaks that appear to correspond are clustered together.

Using custom coded functions, peaks common among the mass spectra are identified using the relatively straightforward clustering algorithm, with specified sensitivity parameters, that is illustrated in FIG. 3.

Referring to FIG. 3, at step 310 a variable maxDist, the maximum allowable distance between peak masses within a cluster, is set. At step 315, massVec, a vector of unique masses from all peaks selected from all spectra, is created and numerically sorted. A preferred embodiment uses a sorting algorithm supplied by R, although those skilled in the art will recognize that other sorting algorithms could be used in this context without deviating from the spirit of the invention. The peaks selected from all spectra are the peaks in the combined data file whose creation is described in steps 210 and 220 (see FIG. 2). At step 220, the counter mCnt, which is used to iterate over the vector massVec, is initialized to 2; a vector growClust is initially set to scalar value massVec[1] and a variable clustDict is initialized as an empty associative array (also referred to as a hash or a list).

At step 325, the counter mCnt is compared to the length of massVec. If mCnt is not greater than the length of (number of elements in) massVec, then at step 330 the value of massVec[mCnt]—massVec[mCnt−1] is compared to maxdist. If the value of massVec[mCnt]—massVec[mCnt−1] is not greater than maxDist, then the peak represented by massVec[mCnt] is assumed to belong to the same peak cluster as massVec[mCnt−1], so at step 335 the element massVec[mCnt] is pushed onto the end of the vector growclust, which already contains massVec[mCnt−1], thereby incrementing the length of growclust by one element. At step 340, the counter mCnt is incremented by 1, and step 325 is repeated.

If at step 330, the value of massVec[mCnt]—massVec[mCnt−1] is greater than maxDist, then the peak represented by massVec[mCnt] is assumed to belong to a new peak cluster, so at step 345 the peak masses corresponding to the previous cluster contained in the vector growClust are added into the cluster dictionary clustDict and given the simple unweighted average of the elements in growClust as the cluster name. At step 350, the variable growClust is assigned the element massVec[mCnt], overwriting the previous contents of growClust. At step 340, the counter mCnt is incremented by 1, and step 325 is repeated.

If at step 325 the value of mCnt is greater than the length of massVec, such that all peak masses have been clustered, then at step 355 the final contents of growClust are added to clustDict as in step 345. At step 360, the cluster dictionary clustDict is used to re-label each peak mass in the data set of all selected peaks created at step 220 (see FIG. 2).

Those skilled in the art will recognize that clustering algorithms other than the one illustrated in FIG. 3 could be used in the subject invention. A standard reference for other methods of cluster analysis is: Kaufman, L. and Rousseeuw, P. J. (1990). Finding Groups in Data: An Introduction to Cluster Analysis. Wiley, New York. Alternate preferred embodiments of the subject invention apply clustering algorithms disclosed in the above reference (or other references known to those skilled in the art), each with its own set of sensitivity parameters to tune, to obtain an acceptable level of unsupervised reproducibility when applied to peak patterns resulting from analysis of different experiments.

Referring again to FIG. 2, once all of the peaks clusters are identified, the mass for each peak in each spectrum is re-labeled as the weighted average of the masses within the corresponding cluster. With the relevant treatment and experimental condition information (e.g., drug, drug concentration, and sample type), cluster average mass, and relative intensity, the data are sufficiently informative for analysis, at step 260.

Analyze Treatment Effects on Relative Peak Intensities: In a preferred embodiment, the primary analysis that is carried out seeks relationships between experimental conditions and relative intensity (chemical abundance) for each peak (chemical) one at a time entity) one at a time and in combination. Examples include, but are not limited to, analyzing the effects of varying drug concentrations for a given drug, comparisons of varying drug concentrations among many drugs, and comparisons of drug response among many biologically and medically relevant sample types and experimental conditions. Using the R programming environment, high level graphics, general linear models, and methods of cluster analysis and pattern recognition are used to identify peaks and peak patterns of interest.

Those skilled in the art will recognize that there are many other ways that this kind of data can be used to address questions of interest in the pharmaceutical and biotech industry. Examples of other contexts in which the disclosed method would be applicable are disclosed in Section 5.6–5.10, infra, and include, but are not limited to, using biologically relevant cell based models and patient samples for the following: (1) simultaneous measurement and analysis of drug impact on entire metabolic pathways; (2) assignment of known and/or unknown drugs and chemical compounds into functional groups based on their overall impact on metabolic activity; (3) identifying new biochemical metabolites or catabolites or pathways; (4) definitions of metabolic peak profiles for drugs and chemical compounds; and (5) patient subgrouping on the basis of basal metabolic profiles and/or profiles in response to drug treatment to permit sensitive customization of treatment regimens; and (6) SAR analysis in combination or not with software like Catalysis (MSI) to perform data mining and or create new active molecules.

The determination of the identity of a peak in the profile can be done in a variety of ways. Molecules which may be present in a biological sample include proteinaceous molecules (including but not limited to glycoproteins, lipoproteins, proteins, polypeptides, peptides, peptoids, and amino acids), nucleic acids (including but not limited to polynucleotides, oligonucleotides, nucleotides, nucleosides, DNA or a derivative, or RNA or a derivative), carbohydrates (including but not limited to polysaccharides, oligosaccharides, and saccharides), lipids (including but not limited to saturated and unsaturated phospholipids, glycolipids, lipopolysaccharides, lipoproteins, cholesterol and analogs thereof, and glycerides) and small molecules (including organic molecules and inorganic molecules). Any of these molecules can be present in their native state or in chemically modified forms.

Comparison of mass spectra of extracts from test samples (e.g., from potentially diseased cells or cells treated with a test compound) compared to controls or reference samples (e.g., from normal or untreated cells) allows the identification of peaks that are increased or decreased (e.g., with the dose of the drugs or the severity of the disease ) as well as peaks that do not vary. Knowing the exact mass of the peak, it could be easy to identify the molecule (either directly in the case of a small molecule or by elucidating the chemical formula of one or more fragments in the case of a large molecule). The first step is to determine the peaks for small molecules. There at least two ways of determining the general formula. First, common elements, including but not limited to C, N, H and O, are used in a linear combination to reconstitute the molecule. As will be appreciated by those in the art, in some cases the molecular mass will take into account an extra proton or an extra atom (for example a sodium atom in the case where the compound is sodiated). Multiple possibilities are evaluated using associated statistical probabilities. A second approach is to search the appropriate databases based on known molecular mass, taking into account isotope abundance. Of the possible candidates, only biological entries will be considered. For large molecules, a fragmentation step is used to enable the identification of the molecule. In addition, the consideration of multiple charged peaks will be used.

Metabolic pathways in biological systems are mostly well characterized and all the identified peaks (molecules) could be positioned on the chart representing metabolic pathways. By identifying a molecule in a metabolic pathway that is altered by a drug or in a disease state it is possible to suggest a mechanism of action therefor. If the molecule is not yet known, its identification could lead to the discovery of a new biochemical metabolite or pathway. Pleiotropic effects may be discovered as well.

In order to elucidate the chemical structure of a large molecule of interest, the molecule is preferably fragmented and the structure of one or more of its fragments identified. However, prior to fragmentation, the nature of the molecule can be determined by one of two approaches.

First is the biochemical approach. The sample of a particular FTMS peak can be treated with an enzyme such as nuclease, which hydrolyzes nucleic acids. The treated sample will again be subjected to FTMS. The absence or presence of the peak will determine whether the sample contains nucleic acids. The sample may be similarly treated with one or more proteases, glucosidases and lipases to determine the presence of proteins, sugars or lipids in the molecule giving rise to the peak of interest. Preferably, multiple classes of enzymes are utilized so that molecules comprising more than one class of components (e.g., glycolipids, lipoproteins) can be so identified protein and sugar. A second method that may occasionally be used is a chemical approach. A sample may be identified by its chemical reactive properties.

Structural elucidation can be carried out in the FTMS instrument by fragmentation of the ion of interest (precursor ion). To do this, an isolation pulse is first used to "sweep-out" all ions except the precursor ion population. Again, advantage is taken of the cyclotron frequency relationship and a rf field is applied which is in frequency with all ions to be ejected from the cell (detector). The ions resonantly absorb this radiation and, with enough power, are excited from the confines of the cell. This leaves only the parent ion trapped within the cell.

The next step is referred to as the ion activation process (fragmentation step). This can in principle be performed using several methods, but that used mostly in FTMS is collisionally activated dissociation (CAD) or infrared-mulitphoton dissociation (IRMPD). The CAD process is accomplished by placing a rf frequency that is in resonance with that of the precursor ion. Enough power is delivered to the ion to excite its cyclotron orbit. Because the ion's frequency is conserved, its angular velocity is increased (i.e. gains kinetic energy). A pulsed valve is triggered to introduce a burst of collision gas into the cell area where the ions are trapped. In addition, as will be appreciated by those in the art, different gases may be used (heavier gases generally produce more fragments). The excited precursor ions have energetic collisions with this gas and this induces fragmentation. Following a brief pumping delay (for the neutrals to be evacuated) the product or fragment ions are detected with all the normal capabilities as described in Section 5.2, supra.

IRMPD (Infrared-Multiphoton Dissociation) is in principle even simpler to implement. The isolated ions are subjected to an intense beam of IR photons. These photons are absorbed and the ions become vibrationally "hot" to the point of activation. The resulting fragmentation products are detected.

Either method produces a fragmentation spectrum (referred to as MS/MS spectrum). This kind of data is instrumental in structure elucidation. For instance, if a precursor ion that consists of one $C_{13}H_{20}N_2O_3$ or $C_{14}H_{24}N_2O_2$ is submitted to a MS/MS experiment, a peak which is 46.005 Da lower in mass from precursor may be observed suggesting that the structure has lost $CH_2O_2$ and contains at least one carboxylate group (i.e. carboxylic acid, sugar, lipid).

The cycle of isolation and fragmentation may be carried over and over to subsequent fragment ions (i.e. MSn). FTMS and other ion trap methods are capable of performing several stages of fragmentation.

Once the entire or a partial amino acid sequence of an isolated protein has been experimentally determined, a computer can be used to search available databases for a matching amino acid sequence or for a nucleotide sequence, including an expressed sequence tag (EST), whose predicted amino acid sequence matches the experimentally determined amino acid sequence. If no matching nucleotide sequence is found, a degenerate set of nucleotide sequences encoding the experimentally determined amino acid sequence can be reverse-engineered by techniques well known in the art; such a degenerate set of nucleotide sequences is useful for cloning the gene that encodes the isolated protein and for expressing the sequenced protein or peptide fragment. Alternatively, if the FTMS peak corresponds to a nucleic acid, the nucleic acid is fragmented and fragments thereof sequenced. Fragment sequences can be used to identify the gene to which they correspond, e.g., Genbank. If the fragment sequence(s) do(es) not correspond to (a) known gene(s), a nucleic acid can be synthetically prepared or amplified by PCR according to methods that are well known to those of skill in the art; see e.g., Methods of Enzymology, volume 152, "Guide to Molecular Cloning Techniques," ed. Berger and Kimmel (Academic Press 1987); Maniatis et al., "Molecular Cloning: A Laboratory Manual," (Cold Spring Harbor Laboratory 1982), both of which are incorporated herein by reference in their entireties. The nucleic acids so generated can be used to screen a genomic or cDNA library to identify the full length gene to which the fragment corresponds. Alternatively, the sequence of the gene or at least an open reading frame thereof, to which the nucleic acid corresponds can be identified by compiling the information obtained by sequencing overlapping nucleic acid fragments of the original HICS-FTMS peak of interest.

Cells genetically engineered to express such a recombinant protein can be used to produce large quantities of the recombinant protein, e.g., for therapeutic administration. Possession of the cloned gene permits gene therapy to replace or supplement a protein whose absence or diminished expression is associated with disease. Possession of the cloned gene likewise permits using antisense or triple-helix therapy to suppress expression of a protein whose presence or enhanced expression is associated with disease or exploiting recombinant expression of the protein in sufficient quantities for immunotherapy, for example, by raising a monoclonal antibody thereto, which can be chimerized (Morrison, et al., 1984, Proc. Natl. Acad. Sci., 81, 6851–6855; Neuberger, et al., 1984, Nature 312, 604–608; Takeda, et al., 1985, Nature 314, 452–454) or humanized (see, e.g., Queen, U.S. Pat. No. 5,585,089 and Winter, U.S. Pat. No. 5,225,539) prior to therapeutic administration.

The FTMS analysis results in a peak profile. A peak profile is the graphical representation of what is detected by the detector of the FTMS, containing a multiplicity of peaks corresponding to the different biomolecules (as well as the different peaks of the same molecule with different isotopes) and fragments of biomolecules as well as multicharged molecules. A peak profile of a particular sample, treated in a particular way, is essentially a "fingerprint" of the state of the sample; while two states may have any particular biomolecule similarly present, the evaluation of a number of biomolecules simultaneously allows the generation of a peak profile that is unique to the state of the cell. This is analogous to the gene expression profile "fingerprints" done on biochips. That is, normal tissue may be distinguished from breast cancer tissue, and within breast cancer tissue, different prognosis states (good or poor long term survival prospects, for example) may be determined. Similarly, peak profiles of lung tissue can be compared against kidney tissue, profiles of breast cancer samples from different patients can be compared, profiles of samples prior, during or after treatment with a drug, or at different drug concentrations, can all be evaluated as described herein.

As will be appreciated by those in the art, these types of comparisons can be done using a single peak profile from the sample, or multiple peak profiles; for example, the sample can be prepared or separated in several ways and the peaks individually analyzed, or overlaid and combined.

By comparing peak profiles of samples in different states, information regarding which biomolecules are important (including both up- and down-regulation) in each of these states is obtained. The identification of biomolecules that are differentially present (including both the appearance or disappearance or changes in peak intensity) allows the use of this information in a number of ways as outlined herein. For example, diagnosis and disease monitoring can be done; the evaluation of a particular treatment regime may be evaluated: does a chemotherapeutic drug act to improve the long-term prognosis in a particular patient. Similarly, diagnosis may be done or confirmed by comparing patient samples with the known peak profiles. Furthermore, these profiles allow screening of drug candidates with an eye to mimicking or altering a particular peak profile; for example, screening can be done for drugs that suppress the breast cancer peak profile or convert a poor prognosis profile to a better prognosis profile.

Thus, the present invention finds utility in a wide variety of applications. In a preferred embodiment, the methods outlined herein are used to analyze samples and build and access databases. In a preferred embodiment, the methods allow the generation of a wide variety of databases, particularly for but not limited to small molecules, since the FTMS allows such high precision.

Thus, in a preferred embodiment, the present invention is used to rapidly identify cellular or sample components. By using FTMS in conjunction with other computation chemistry software, such as MSI CATALYST, rapid identification and characterization of new active molecules can be done. CATALYST is a program that explores the possible active shape of drug candidates. By running a small library of compounds and looking for desirable spectrum attributes, a "pharmacophore description" can be generated using CATALYST or similar programs. This "description" can then be used to screen virtual libraries to generated additional candidates which can then be tested.

In addition, it should be noted that quantification and comparison of different spectra can be done in a variety of ways. In one embodiment, the sample is electrosprayed (with the use of a double spray source being preferred), along with a simultaneous spray of a reference sample, to allow quantification and comparison. Alternatively, the reference is added to the sample. Finally, another alternative is to normalize using components known to be roughly equal in the samples in question, for example using different cellular housekeeping genes or proteins or metabolites that are under homeostasis.

Thus, by running large numbers of samples from a variety of different sources and under different conditions, databases of data are generated. These can be used in a variety of ways. In a preferred embodiment, the databases are used in further experiments to identify peaks. Alternatively, they can be used to compare samples or the effects of drugs or candidate agents on samples, to identify signaling pathways and therapeutically relevant components.

In addition, when the databases are generated, they may be visualized using any number of graphical representation software, including visualization software such as SPOTFIRE®, 3D contour mapping, topology mapping, triangulation techniques, etc.

The present invention provides methods for analyzing a complex biological sample, comprising the steps of subjecting the sample to FTMS, which provides a peak profile of the sample, and evaluating the peak profile of the sample. In one embodiment, the methods further comprise comparing the peak profile of the sample with a peak profile of a reference sample. Accordingly, the biological sample can be a test sample. The reference sample can be predetermined, i.e., is a historical sample. The peak profile of the reference sample can be the peak profile of one sample or an average peak profile for two or more samples. In one embodiment, the reference sample is derived from a normal cell and the test sample from a diseased cell of the same type. In another embodiment, the reference sample is derived from a diseased or normal cell and the test sample derived from a diseased cell after the diseased cell has been exposed to a biomodulator such as a drug or hormone.

The present invention further provides methods for detecting a response of a cell to a biomodulator, comprising comparing an FTMS peak profile of a first biological sample derived from a cell that has not been exposed to the biomodulator to an FTMS peak profile of a second biological sample derived from a cell that has been exposed to the biomodulator.

The present invention further provides methods for identifying a marker of a response of a cell to a biomodulator, comprising detecting a response of cell to the biomodulator according to the method of claim as described herein, and identifying a peak that differs in intensity between the peak profiles for the first and second biological samples, which peak does not correspond to the molecular mass of said biomodulator, wherein a peak so identified corresponds to a marker of a response of the cell to the biomodulator.

The present invention further provides methods for characterizing a marker of a response of a cell to a biomodulator, comprising identifying a marker of a response of a cell to a biomodulator according to the methods described herein, isolating a marker ion having the m/z ratio of said marker; and obtaining the molecular sequence or chemical structure of said ion or a fragment thereof.

The present invention further provides methods for identifying a molecule whose concentration in a cell changes when the cell is contacted with a biomodulator, comprising comparing an FTMS peak profile of a first biological sample derived from a cell that has not been exposed to the biomodulator to an FTMS peak profile of a second biological sample derived from a cell that has been exposed to the biomodulator, and identifying a peak that differs in intensity between the peak profiles for the first and second biological samples, which peak does not correspond to the molecular mass of said biomodulator, wherein a peak so identified corresponds to a molecule whose concentration in a cell changes when the cell is contacted with a biomodulator.

The present invention further provides methods for identifying at least one marker of a disease or condition, comprising comparing an FTMS peak profile of a first biological sample derived from a normal cell to an FTMS peak profile of a second biological sample derived from a cell having the disease or condition, and identifying a peak that differs in intensity between the peak profiles for the first and second biological samples, wherein a peak so identified corresponds to a marker of said disease or condition.

The present invention further provides methods for diagnosing a disease or condition in a patient, comprising identifying (at least one) a marker of said disease or condition according the methods described herein, and determining the intensity of the peak corresponding to said marker in a biological sample obtained from a cell of said patient, wherein the intensity of the peak is indicative of the presence or extent of the disease or condition in said patient.

The present invention further provides methods for monitoring the efficacy of a therapeutic treatment in a patient suffering from a disease or condition, comprising identifying a marker of said disease or condition according the methods described herein; and determining the intensity of the peak corresponding to said marker in a biological sample obtained from a cell of said patient after the patient has been subjected to the therapeutic treatment, wherein the intensity of the peak is indicative of the presence or extent of the disease or condition in said patient and a reflection of the efficacy of said therapeutic treatment.

The present invention further provides methods for identifying a lead molecule for drug development, comprising identifying a marker of a disease or condition according the methods described herein, for which disease or condition the identification of a lead molecule for drug development is desired, obtaining an FTMS peak profile of a sample derived from a cell having a concentration of said marker characteristic of the disease or condition, said sample being derived from said cell after the cell has been exposed to a test molecule, and determining whether cell the concentration of said marker is altered by the test molecule, said determining comprising measuring the intensity of the peak to which the marker corresponds, wherein a change in the concentration of said marker, said change approximating the normal levels of said marker, indicates that the test molecule is a lead molecule for drug development for the treatment or prevention of said disease or condition.

In addition, the present invention can be used in lead compound development in structure-activity relationships (SAR). Thus, the analysis of the spectra from related compounds can serve to correlate the structure of the compound to its desired activity.

The present invention further provides methods for identifying toxicological targets of drugs, comprising comparing three FTMS peak profiles, wherein the three FTMS peak profiles correspond to a first biological sample obtained from a cell which has been exposed to a first drug with a toxic side effect; a second biological sample obtained from a cell which has been exposed to a second drug without a toxic side effect, wherein the first drug and the second drug belong to the same class of drugs; and a third biological sample obtained from a cell which has not exposed to any member of said class of drugs; and identifying a peak that is similar in intensity between FTMS profiles of the second and third samples but differs in intensity in the FTMS profile of the first sample, wherein a peak so identified is correlated to a toxic effect for drug development.

The present invention further provides other methods for identifying toxicological targets of drugs, comprising comparing three FTMS peak profiles, wherein the three FTMS peak profiles correspond to a first biological sample obtained from a cell which has been exposed to a first drug with a toxic side effect; a second biological sample obtained from a cell which has been exposed to a second drug having the same toxic side effect; and a third biological sample obtained from a cell which has not exposed to any drug having said toxic side effect; and identifying a peak that is similar in intensity between FTMS profiles of the first and second samples but differs in intensity in the FTMS profile of the third sample; wherein a peak so identified is correlated to a toxic effect for drug development.

The present invention further provides methods for characterizing the toxic properties of a test agent comprising determining the intensity of a peak in an FTMS peak profile of a biological sample obtained from a cell which has been exposed to said test agent, said peak having been identified as a toxicological target by one or more of the methods described herein, wherein the intensity of the peak is indicative of the toxicity of the test agent.

The present invention yet further provides methods for high information content (HIC) analysis of a complex biological sample, comprising subjecting the sample to a plurality of instances of Fourier Transform Mass Spectrometry (FTMS); and for each instance of FTMS, generating FTMS peak profile information for the sample; applying a peak picking algorithm to the generated peak profile information to select peaks that satisfy given criteria; and applying a clustering algorithm to the selected peaks to identify peaks likely to correspond to the same chemical entity.

In one embodiment, the peak profile information is written into a separate file for each instance of FTMS, and further comprising the step of creating a single file that comprises information from each of said separate files for the peaks selected by the peak picking algorithm. In one mode of the embodiment, the clustering algorithm is applied to information contained in said single file comprising information from each of said separate files for the peaks selected by the peak picking algorithm.

In another embodiment, each of the selected peaks is re-labeled with the average of masses from a corresponding cluster of peaks.

The present invention provides methods for generating FTMS spectra of complex biological samples and analyzing the peak profiles in the spectra. Complex biological samples include samples derived from biological material that includes but is not limited to blood serum, cultured cells, tissue biopsies. Comparative analysis of spectra generated for cells in different states or of different types is useful for specific phenotypic differences existing between normal and abnormal, for example non-diseased and diseased, cells and/or tissues of the same type. Furthermore, once specific phenotypic differences have been identified in the form of FTMS peaks of differential intensity, the molecules to which the peaks correspond can be identified and/or be used as lead biomolecules for diagnostic and/or pharmaceutical development.

The methods of the present invention further encompass identifying a peak or pattern of HICS-FTMA peaks that are characteristic of a particular pathology or class of pathologies. Such peak profiles provide valuable information useful for more fully and precisely defining and classifying pathology subtypes.

Utilizing the principles of the present invention, samples from many different patients having known health conditions can be collected and subjected to HICA-FTMS. The profiles generated are analyzed to identify peaks that are uniquely present or absent in samples derived for cells of patients having different health conditions, and the resulting data are used to create a database incorporating all of the peaks so identified. Data relating to samples obtained from patients exhibiting a pathology or disease of interest may then be extracted for analysis and compared with the remaining records in the database to identify peaks or peak patterns of interest that would be predictive of the pathology or disease state.

In certain embodiments, HICA-FTMS, therefore, is a tool to generate peak profiles and identify a pattern of molecular peaks, or marker peaks, that is characteristic of a particular pathology or class of pathologies. Monitoring the intensities of marker peaks, representing the relative amount of the marker molecules to which the peaks correspond, in peak profiles generated from the same sample source under different conditions or time points can be used in monitoring progression of response to therapy of a disease and target-driven drug discovery for the disease.

Utilizing the principles of the present invention, tissue or cell samples from experimental animals that are models for a disease treated with one of the known therapeutics used in the management or treatment of the disease, or biological samples from humans undergoing these treatments or a cell culture model thereof, can be subjected to HICS-FTMS, and the resulting data used to create a database incorporating all of the common and unique peaks that are either present or absent in samples of treated subjects (animal model or human) by comparison with their untreated counterparts. Marker molecules corresponding to marker peaks can be used as targets for the development of a therapy or pharmaceutical. Similarly, peak profiles of biological samples derived from normal plants can be compared to peak profiles of biological samples derived from plants treated with phytosanitary drugs, weed killers or hormones, or from plants infected with pathogens such as viruses. Marker molecules that corresponding to marker peaks identified in these screens can be targets for the development of insecticides. Also similarly, peak profiles of biological samples derived from microorganisms that have been treated with antibiotics can be compared to peak profiles of biological samples derived from untreated microorganisms of the same species, for example to identify marker molecules of antibiotic resistance that can be used as drug screening markers.

In addition to monitoring drug responses, HICS-FTMS can be employed to monitor the drug, itself. Thus, particular attributes of a target drug can revealed, such as clearance profiles, molecular interactions and modifications, drug metabolism, mode of action, and subcellular localization.

The present invention provides methods of identifying new drugs that are useful in the treatment of a disease or disorder for which a current drug is already known, for example to identify a drug with increased efficacy, higher tolerance. HICS-FTMS spectra are generated for extracts of cell, tissue or cell culture samples that are (i) untreated, (ii) treated with the known drug, or (iii) treated with a test molecule. Test molecules that elicit changes in the FTMS peaks similar to those seen in extracts of cell culture samples that have been treated with the known drug are then candidate lead compounds for drug discovery. Wherein cultured cells or tissues are utilized in the practice of the present invention, for example as a model system for drug discovery, the cells can be isotopically depleted or enriched, to facilitate characterization and sensitivity.

The screening assays of the present invention allow the identification of peaks that are targets of individual drugs and of common peaks present in samples from cells that have been exposed to or organisms that have undergone treatment with different members of a class of drugs of interests, e.g., anti-hyperlipidemic drugs. At the same time, target peaks that are present or absent in samples treated only with one drug or a subset of the class of drugs can be noted, and these peaks correlated with activities that are unique to that drug(s). An increase or decrease in the intensity of such a peak can correlate with desirable activities or properties of the drug(s), for example a glucose-lowering activity in an anti-hyperlipidemic drug, or an undesirable activity or property, such as the tendency to induce nausea or dizziness as a side effect of treatment. This information can be used in the discovery of drugs that, upon exposure to biological systems, elicit only the desired responses.

Certain drugs will exert their effects through a large number cellular targets, whereas others with more limited effects will only influence few targets. Similarly, some drugs will exert their effects on multiple cell types whereas others will only affect one or a few cell types.

There are a number of examples outlined below.

Metabolic Syndrome or Syndrome X is manifested by defective glucose metabolism (insulin resistance), elevated blood pressure (hypertension), a blood lipid imbalance (dyslipidemia, including levels of circulating high triglycerides and low levels of circulating "good", or HDL-, cholesterol) and central obesity (excessive fat tissue in the abdominal region) (see, e.g., Reaven, 1993, Annu. Rev.

Med. 44:121–131). Syndrome X patients are presently administered separate drugs to treat the individual symptoms, because commercially available drugs have been optimized to modulate one specific target or regulate one specific parameter of a disease state. The use of multiple drugs increases the risk of serious side effects and compromises the quality of life. HICS-FTMS can allow the identification of new drugs that have multiple, simultaneous therapeutic effects. This is virtually impossible using HTS approaches based on single targets.

The number of Syndrome X patients is rapidly increasing and seems to be associated with the Western lifestyle; particularly high risk factors are age and diet. Syndrome X drugs having pleiotropic effects, i.e., drugs that control multiple or preferably all symptoms of Syndrome X, are urgently needed.

HICS-FTMS also allows the identification of marker molecules that are tissue-specific, which can be used as markers for subsequent screening for tissue-specific drugs. Such drugs would have great utility in therapeutic regimens. For example, insulin-resistant diabetics are given thiazolidinedione (TZD) drugs to manage their disease. TZDs activate the peroxisome proliferator activated receptor gamma (PPARγ). Insulin sensitization is increased following treatment with TZDs, but so does adipose tissue fat deposition. Recently, a lead TZD, Rezulin, was recalled because of the serious side effect of liver disease, marked by jaundice, nausea, vomiting, abdominal pain, fatigue, lack of appetite, and dark urine, leading to death and/or the need for liver transplants. HICS-FTMS is a method of choice to screen for and identify drugs that, like TZDs, promote insulin sensitization, yet unlike TZDs do not lead to liver disease.

In another embodiment, wherein a drug exerts its effects through multiple targets, HICS-FTMS enables the characterization of improved analogs. Molecules can be identified that exert those same effects more effectively and/or with reduced non-specific effects, faster clearance. Essentially, HICS-FTMS peak profiles are generated for samples exposed to a known drug or class of drugs, and peaks that are correlate to the therapeutic properties of the drug identified. Combinatorial chemistry can be used to generate libraries of analogs of the drug, and these analogs can be used in HICS-FTMS assays using the experimental model as was used to identify the beneficial peaks associated with the parent drug. Analogs with higher efficacy than the parent drug, for example those that affect the target peaks at lower concentrations than does the parent drug, are then used as lead compounds for drug development.

In certain embodiments of the present invention, drug discovery is achieved without comparison to known drugs, purely based on a test molecule's ability to elicit specific changes in FTMS peak profiles at very low concentrations (in the nanomolar range). The identity of the peaks affected by the test molecule is then identified, as described in Section 5.5, supra, which may provide guidance as to which pathway the test molecule modulates, and therefore which diseases the test molecule may be test as a drug for. In vivo testing of the test molecule can initially carried out using a cell culture model, preferably using a cell representative of a disease state (e.g., tumor cell line), or in an animal, preferably in an animal model for the disease, most preferably in rats or mice, before progressing to clinical trials. Drugs for use as antibiotics can be tested on bacterial cultures. Plant drugs (e.g., antivirals) can be tested in a controlled laboratory setting before release into the ecosystem.

There are several common sources of lead compounds (drug candidates), including natural product collections, synthetic chemical collections, and synthetic combinatorial chemical libraries, such as nucleotides, peptides, or other polymeric molecules.

The test molecules of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Bio/Techniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865–1869) or phage (Scoff and Smith, 1990, Science 249:386–390; Devin, 1990, Science 249:404–406; Cwirla et al., 1990, Proc. Natl. Acad. Sci. USA 87:6378–6382; and Felici, 1991, J. Mol. Biol. 222:301–310).

The methods of the present invention can be applied to the selection of patients for treatment by a drug.

Samples from such individuals, for example, can be subjected to HICS-FTMS to determine whether a peak associated with a particular sensitivity or resistance to a drug or allergy to a class of drug is present in or absent from their FTMS peak profiles. A peak associated with a particular sensitivity to a drug is predetermined by comparing the HICS-FTMS spectra of individuals treated with the drug or class of drugs and identifying those peaks whose relative intensity correlates with a sensitivity or resistance to treatment.

The methods presented herein can be used to determine the optimal dose of a drug. The HICS-FTMS peak profiles of extracts of cells treated with different concentrations of a drug are compared for the intensities of one or more peaks that correspond to a favorable response to the drug, for example of a target molecule of the drug. The same peak profiles are also analyzed to determine the intensities of one or more peaks associated with an unfavorable response to the drug, for example toxicity. A dose or range of dosages at which the drug elicits a maximal favorable response with minimal toxicity is thereby identified.

HICS-FTMS technology can be also used generally to characterize cellular or organismal responses to signaling molecules, such as hormones, growth factors, cytokines, and neurotransmifters. Thus, a comparison of peak profiles derived from samples comprising cell extracts of cells treated with a particular growth factor can demonstrate a pattern associated with the growth factor. Time course studies can be conducted, for example to investigate peaks associated with early vs. late responses to the growth factor.

Identification of distinctive peaks results in the identification of markers, and subsequent chemical elucidation of the corresponding ions ultimately may aid in pharmaceutical design.

Similar to the application of HICS-FTMS to the study of diseases, biological responses to the introduction of a genetic perturbation can be assessed at the cellular or organismal level. A genetic perturbation can be a hypomorphic, hypermorphic or neomorphic mutation in a native gene, recombinant overexpression of a native gene that can be normally expressed or not expressed in a the cell of interest, recombinant expression of a foreign gene, the use of antibodies against a gene product, the introduction of antisense nucleic acid or triple helix molecule that would inhibit the gene. Comparisons of the peak profiles of extracts of cells that are wild-type, heterozygous and/or homozygous for a gene, and/or overexpression of the gene, can yield useful information regarding the genetic locus, such as biochemical pathways in which the gene is involved, the extent of perturbation of the system as a result of the perturbation of the gene, cellular targets of the mutated gene product (e.g., receptors, enzymatic complexes, substrates). The gene suffering the mutation need not be identified beforehand, such that the HICS-FTMS method screens for unknowns that, as a result of the mutation, affect an array of molecules of interest. The method is equally applicable where the mutation is naturally occurring.

In a particular application, HICS-FTMS can be used to monitor food or food products of plant or animal sources. Peak profiles of each product can be obtained to serve as a reference for quality-control tests, or to ensure integrity of the stock by monitoring genetic variation over time. Similar to the drug screening tests, HICS-FTMS can be used to select and maintain favorable traits, while identifying unwanted traits.

This technology also has potential application at the systemic level, such as aquatic ecosystems, soil compositions, and atmospheric systems. These complex biological systems can be characterized by HICS-FTMS, and peak profiles taken over time so as to monitor either natural changes or changes due to human intervention.

The present invention greatly facilitates the field of diagnostics. In one embodiment, a patient's serum sample can be subjected to HICS-FTMS, and the peak profile or "peak profile" thereby generated would provide a snapshot of the patient's serum parameters that would otherwise require individual testing. Individual peaks known to represent parameters of interest are compared to a corresponding range of peaks from normal individuals to determine their concentration in the serum. Parameters that can be assayed include but are not limited to cholesterol, fatfy acids, lipoproteins, glucose, hemoglobin, cytokines, hormones (e.g., , insulin, TSH, T4, T3), antibodies (e.g., for autoimmune diseases such as systemic lupus erythematosus, Hashimoto's disease), tumor antigens (e.g., PSA).

In another embodiment, cerebrospinal fluid of a patient is tested for the presence or intensities of markers of neurodegenerative disorders such as Alzheimer's Disease, Parkinson's Disease, prior diseases, frontotemporal dementia. Certain markers for these diseases are already known (e.g., phosphorylated tau protein or the 42 amino acid form of the $A\beta$ (Amyloid $\beta$) peptide in Alzheimer's Disease), and additional markers or marker peaks can be identified by the methods disclosed herein. A marker peak can be a peak whose intensity increases or decreases with the progression of a neurodegenerative disorder.

The methods of the present invention may also be applied to monitor the progress of a disease in a patient or the patient's response to treatment. Multiple HICS-FTMS peak profiles of the patient's samples (serum, tissue biopsy) are generated following indications of a high risk of a disease or the patient's diagnosis with a disease (with or without treatment). For example, a person with intermediate levels of one or more neurodegenerative disorder-associated markers, which levels are insufficiently high to signal a disease state yet are above average, can be monitored periodically to determine if the marker peaks rise to a level indicative of a disease state so that treatment can commence. Alternatively, a patient having been diagnosed with a disease can be monitored to determine the efficacy of the medication (if on treatment) or the progression of the disease (if the disease is incurable), for example by monitoring for the levels of neurodegenerative disorder-associated antigens following diagnosis with a neurodegenerative disorder.

HICS-FTMS can be used generally to characterize toxicological consequences of drug treatments. For example, an HICS-FTMS peak profile can be obtained from a test subject experiencing a particular type of drug side-effect. Peak profiles of every known drug that produces a substantially similar side-effect can be compared to discover patterns which may prove diagnostic or characteristic to a particular toxicological side-effect. This analysis may be extended so as to characterize side-effects caused by combination therapies whose HICS-FTMS peak profiles may be predictive of undesirable drug combinations. Furthermore, peak profiles may be obtained for many different dosages of a specific drug, so as to afford predictive capability regarding appropriate dosage.

Test subject can be humans, laboratory animals, cell cultures, yeast models, bacterial models, cell-free systems, or other in vitro systems.

Peak profiles may be obtained by analyzing biopsies, tissue explants, cell cultures, or bodily fluids. The toxicological markers need not be found in cells or tissues in which the drug exerts its therapeutic effect. For example, although a drug may have a localized effect, the drug's toxicity may be due to its metabolites which could be found in the liver, bloodstream and/or urine.

Given the HICS-FTMS peak profiles that characterize a particular side-effect, specific peaks can be designated as toxicological markers for that side-effect. These markers can serve as a rapid diagnostic method. Furthermore, identification of these markers may elucidate the toxicological pathways and thus ultimately be useful for design of therapeutics. Certain markers may be present only in a subset of subjects, reflecting individual sensitivities to medications. This variability in drug sensitivity can be exploited to further define toxicological markers for different subgroups.

Construction of HICS-FTMS peak profiles at multiple timepoints throughout a course of treatment may identify intermediate stages in a toxicological episode. Thus, not only may characteristic HICS-FTMS peak profiles be found for the end-points (side-effect versus no side-effect), but HICS-FTMS peak profiles may allow for identification of several intermediate stages towards either end-point. These discernible intermediate stages then could be used to monitor toxicological effects and its subsidence during a treatment regimen.

Once a database of HICS-FTMS-generated spectra of various drug responses has been created, a HICS-FTMS peak profile obtained from a test subject exposed to a novel drug or new treatment regimen may predict potentially adverse side-effects. Thus, treatments or dosages could be adjusted before administration.

The practical utility of this technology can be exemplified by a course of treatment for lowering serum cholesterol.

Many drugs have been used in the treatment of high serum cholesterol, including bile-acid-binding resins (e.g., cholestyramine (Questran Light®, Bristol-Myers Squibb), colestipol hydrochloride (Colestid®, The Upjohn Company), statins (e.g., Lovastatin (Mevacor®, Merck & Co., Inc.), pravastatin (Pravachol®, Bristol-Myers Squibb Co.), atovastatin (Parke Davis)), nicotinic acid, fibrate (e.g., clofibrate (Atromid-S®, Wyeth-Ayerst Laboratories)), gemfibrozil (Lopid®, Parke-Davis), oral estrogen, long chain carboxylic acids (e.g., long chain α,ω-dicarboxylic acids, β,β,β',β'-tetrasubstituted-α,ω-alkanedioic acids). Unfortunately, these medications have been associated with numerous side-effects, including gastrointestinal disorders, selective vitamin deficiencies, liver and kidney dysfunction, cancer, gallbladder disease, thromboembolic disease, hepatic adenoma, rabdomyolysis, elevated blood pressure, glucose intolerance, and hypercalcemia. Many other molecules that have in vivo and/or in vitro activity, including lead compounds for anti-hypercholesterolemic drug development, have been never been exploited in therapeutic regimens for a variety of reasons. Therefore, there is a clear need to develop therapeutics that lack side-effects, yet combat high serum cholesterol and diseases resulting from undesirable lipid metabolism.

HICS-FTMS peak profiles could be obtained for each treatment regimen and for each pre-clinical compound having the desired activity. Comparison of the peak profiles among treatments may distinguish certain peaks associated with the deleterious effects of the drug. These distinctive peaks may provide an assay for screening out compounds offered for use in treating high serum cholesterol that have unwanted side-effects. Moreover, identification of the compounds represented by these peaks may provide clues to drug design that would avoid side-effects. Further investigation by HICS-FTMS of the time course of drug treatment may reveal mode of action or indicate novel points for intervention.

A strategy similar to that proposed for studying drug toxicology could be adapted for deleterious biological responses to carcinogens, poisons, and radiation. Characteristic peak profiles of responses to these agents can be determined, compared to untreated samples to identify marker peaks, and then used to monitor biological responses or screen unknowns for potentially adverse agents. Once characteristic peaks are identified, a test agent of unknown properties can be assayed, for example for its carcinogenicity, by determining the extent, if at all, that the agent can enhance or inhibit the peak(s) of interest.

HICS-FTMS has the capacity to characterize virtually all molecular differences occurring between normal and diseased cells and/or tissues of the same type, or between cells treated with a test molecule such as a drug and their untreated counterparts. The HICS-FTMS methods of the present invention provide much more information than existing target discovery methods such as genomics or differential expression techniques that focus on detecting genotypic changes and detect only DNA or mRNA changes; moreover, proteomics do not detect non-protein drug or disease target, and therefore only relate to proteins encoded for by the particular sequences. There are presently no methods available by which the differences in metabolite content of cells can be assessed. By contrast, the methods of the present invention allow the detection of all types of drug or disease targets, whereby the targets could be proteins, small peptides, carbohydrates, nucleic acids, metabolites, or any molecules having a mass or structure that is capable of being detected by FTMS. The information produced by HICS-FTMS can be compiled into databases, for use as reference points in future HICS-FTMS screens, for complex comparisons of large numbers of peak profiles.

The methods of the present invention can further be used to monitor cellular or organismal responses to stress and identify key components that can be used as targets for the discovery of agents that either mimic or inhibit stress responses. As used herein, stress refers to any type of insult to the environment or integrity of a cell or organism. Such insults include but are not limited to extreme temperatures, emotional stress (fright, shock), wounds, nutrient deprivation, metabolic responses, infection with intracellular pathogens, and oxygen radicals.

Briefly, FTMS peak profiles are obtained for cells or organisms in their normal states and at various time points following exposure to injury. Peaks that are present at significantly higher levels in the injured cells are potential effectors of the cellular or organismal response to the injury. Once an effector is identified, HICS-FTMS or rational drug design can further be used in the discovery of analogs/agonists and antagonists of the effector. If the response is beneficial (for example, natural plant insecticides produced in response to a pest attack), analogs or agonists of the effector may be developed for treating or preventing future insults. If the response is deleterious (for example, anaphylactic shock in response to an insect bite), antagonists of the effector may be developed to prevent the adverse response upon future insults. Drugs so identified can be tested for their efficacy in modulating the responses animal models that are exposed to the same insults.

EXAMPLES

Methods and Instrumentation

Isolation and Testing of Primary Rat Hepatocyte Cells with Lovastatin

A male Sprague-Dawley rat was anesthetized by administration of sodium pentobarbitol by at 50 mg/kg body mass be intraperitoneal injection. In situ perfusion of the liver was performed as follows. The abdomen of the animal was opened, the portal vein was cannulated, and the liver perfused with WOSH solution (149 mM NaCl, 9.2 mM Na HEPES, 1.7 mM fructose, 0.5 mM EGTA, 10 μU/ml heparin, pH 7.5) at a flow rate of 30 ml/min for 6 minutes. To digest the liver, DSC solution (6.7 mM KCl, 143 mM NaCl, 9.2 mM Na HEPES, 5 mM $CaCl_2$—$2H_2O$, 1.7 mM fructose, 0.2% BSA, 100 U/ml collagenase Type I, 80 U/ml, 160 BAEE/ml trypsin inhibitor, pH 7.5) was perfused through the liver at a flow rate of 30 ml/min for 6 minutes at a temperature of 37° C. After digestion, cells were dispersed in a solution of DMEM– (DMEM containing 2 mM GlutMax-1, 0.2% BSA, 5% FBS, 12 nM insulin, 1.2 μM hydrocortisone) to stop the digestion process. The crude cell suspension was filtered through three layers of stainless steel mesh with pore sizes of 250, 106, and 75 um respectively. Filtered cells were centrifuged at 50×g for two minutes and the supernatant discarded. The cell pellet was resuspended in DMEM– and centrifuged again. This final cell pellet was resuspended in DMEM+HS solution (DMEM containing 2 mM GlutMax-1, 20 nM delta-aminolevulinic acid, 17.4 mM MEM non-essential amino acids, 20% FBS, 12 nM insulin, 1.2 uM hydrocortisone) and plated to form monolayer cultures at a density of $100 \times 10^3 cells/cm^2$ on collagen coated culture dishes. Four hours after initial plating, media was changed to SF-DMEM+ (DMEM containing 2 mM GlutMax-1, 20 nM delta-aminolevulinic acid, 17.4 mM MEM non-essential amino acids, 12 nM insulin, 1.2 μM hydrocortisone) and remained on cells overnight.

To evaluate the effects of lovastatin on hepatocyte cells, cells were exposed to increasing concentrations ranging from 0.03 to 30 µM for 4 hours. Control cells were exposed to the same media lacking lovastatin. To prepare media containing lovastatin, a 30 mM lovastatin solution in dimethylsulfoxide was prepared under aseptic conditions. In a sterile biosafety cabinet the 30 µM concentration was prepared by diluting the stock DMSO formulation 1:1000 in SF-DMEM+. Lower concentrations were prepared by dilution of the 30 µM stock with 0.1% DMSO in SF-DMEM+. To treat cells, the media was removed and 100 µL per well of formulated lovastatin was added. Cells were incubated for 4 hours at 37° C. in humidified 95% air /5% $CO_2$ environment. At the completion of the incubation, media was removed and extracted on ice with 2 volumes of methanol:water:acetic acid (MeOH:DIW:HAc;49:49:2). Cells were extracted 3 times with 200 µL each of MeOH:DIW:HAc. Salts were removed from both media and cell extracts with cationic resin AG® 50W-X9 (Bio-Rad Laboratories, Hercules, Calif.). To remove the resin, samples were centrifuged at 1000 rpm and supernatants were transferred to HPLC sample vials.

FTMS of Extracts of Rat Hepatocytes Treated with Lovastatin

All measurements were carried out on a Bruker APEX II FTMS equipped with a 7.0 Tesla magnet. Culture media and cells were extracted by different solvents, transferred to individual sample vials and placed in a tray for autosampling. A Gilson 215 liquid handler was used for autosampling all 200 wells. Control of the Gilson 215 was managed through the XMAS S package, which also acts as the main software platform for controlling the FTMS spectrometer. Accurate mass detection was performed with the use of external calibration. The mass spectrometer was calibrated prior to the autosampling run using a mixture of standard peptides. The accurate mass data was then analyzed using TcI/Tk routines, which serially search the mass spectra from each well for chemical composition of metabolic products.

Results

After accurate FTMS spectra were collected and analyzed, HICS-FTMS Data Analysis Software (described in Section 5.3.1, supra) was used to select, compare and analyze peaks from the spectra. Sample portions of the spectra generated are shown in FIG. 4, with arrowheads indicating exemplary peaks whose intensities were amplified with lovastatin treatment.

HICS-FTMS Data Analysis Software was used to analyze FTMS spectra data of samples of hepatocytes treated with different concentrations of lovastatin. 82 low molecular mass peaks were selected and further analyzed in graphic format, which is represented as the relative intensity of the peak at each concentration of lovastatin (normalized against the measurements obtained from untreated animals vs. the concentration in µM (see FIGS. 5a–5h). LOWESS, a robust local fitting procedure, was used to perform linear and non-linear curve fitting. Logistical regression was also used to refine the curve fitting and provide accurate statistical measures; linear regression can also be used for this purpose.

Some graphs showed a good correlation between the concentration of lovastatin and the relative intensity, while others showed little correlation. Graphs showing little or no correlation may be artifactual and are of little interest at this point. The molecules of practical significance are the ones showing a strong correlation between the concentration of the drug and the relative intensity. Such peaks of interest may increase or decrease linearly or sigmoidally with drug concentration. These peaks may be considered the most relevant for the therapeutical activity, toxic effects and/or other biological effects in that context.

One aspect of the result worth noting is the sensitivity of FTMS in separating peaks in this complex cellular system. For example, two peaks at molecular masses of 85.02815 and 85.64405 were identified, a difference in mass of 0.7%. While the peak at molecular mass 85.02815 showed a decreasing trend at increasing lovastatin concentrations, the peak at molecular mass 85.64405 showed an increasing trend. Clearly two molecules of different but close molecular masses were affected by the drug in two different ways, and these differences were successfully resolved by HICS-FTMS.

Discussion

The data demonstrate detection both treatment-dependent and -independent changes in intracellular and extracellular components. The abundance of parent compound and several metabolites correlates to variations in the abundance of other small molecules present in the wells. Furthermore, the mass accuracy demonstrated for each of the samples (<2 ppm) provides unambiguous information on the structure and formulae for metabolic products.

HICS-FTMS Applications to Monitoring Biological Responses in Serum Three rats were treated daily with 100 mg/kg of 6-(6-hydroxy-5,5-dimethylhexyloxy)-2,2-dimethylhexan-1-ol by oral gavage, over the course of one week. 6-(6-hydroxy-5,5-dimethylhexyloxy)-2,2-dimethylhexon-1-ol increases HDL-cholesterol and improves glucose utilization in experimental rats (see U.S. application Ser. No. 09/540,738, filed Mar. 31, 2000). At the end of the week, blood was drawn from each of the three rats, as well as from three control (untreated) rats. The blood was allowed to coagulate, and the plasma was prepared for FTMS by adding a water and methanol solution (49:49:2, water:methanol:acetic acid v:v:v) each of the plasma preparations. The mixture was chilled to precipitate the proteins to the bottom of the tube. Each tube was centrifuged, the supernatant decanted and the sample desalted by adding approximately 100 mg of DOWEX ion exchange resin to each vial and incubating the sample with the resin for approximately 10 minutes. The sample was then centrifuged and the supernatant removed. This solution was then introduced to the FT mass spectrometer.

A selected region of the peak profile for the samples is shown in FIG. 6. FIG. 6A–C are spectra of samples derived from the plasma of untreated rats, while FIG. 6D–F are spectra of samples derived from the plasma of rats treated with 6-(6-hydroxy-5,5-dimethylhexyloxy)-2,2-dimethylhexan-1-ol. At least two peaks corresponding to molecules of molecular mass of approximately 766.4 and 766.8 Daltons are of reproducibly higher intensities in the spectra of samples derived from the plasma of 6-(6-hydroxy-5,5-dimethylhexyloxy)-2,2-dimethylhexyloxy)-2,2-dimethyl-1-ol-treated rats.

This experiment demonstrates the utility of the methods of the invention in screening for markers of biological responses to drugs in biological material obtained from mammalian tissue.

Identification of Novel Anti-diabetic Drugs

Insulin resistance and Syndrome X prevalence is increasing in the population. Clustering of insulin resistance, hypertension, hypertriglyceridemia and low plasma HDL cholesterol are hallmarks of Syndrome X (Cornicelli, 1997, Atherosclerosis 2(2):43–49).

Several drugs are available for treating Syndrome X patients, including sulfonylurea drugs, biguanides and TZD derviatives. Sulfonylurea drugs are reasonably well tolerated, but after several years of treatment the ability of the drugs to control glucose markedly decreases. Biguanides are widely used but can induce serious side effects, e.g., lactic acidosis and gastrointestinal disorders. TZD derivatives induce body wight gain and liver failure. Drugs that are presently under development for the treatment of Syndrome X related disorders are prevalently nuclear receptor ligands/activators. Several studies in vitro and in vivo have demonstrated that PPARγ agonists reduce triglycerides and increase insulin sensitization.

TZDs are PPARγ activators. Other drugs useful for treating Syndrome X -by regulating cholesterol and bile homeostatis, adipocyte function and glucose metabolism- activate other nuclear receptors, e.g., RXR (retinoic acid receptor), FXR (bile acid receptor), LXR (oxysterol receptor).

Human hepatocyte, enterocyte, adipocyte and muscle cell cultures are independently treated with (i) compounds useful for managing at least one aspect of Syndrome X in humans (for example, drugs effective in decreasing triglycerides and LDL cholesterol as well as increasing HDL, e.g., fenofibrate, bezafibrate and gemfibrozil); (ii) compounds known to be active in vitro and have been validated in an animal model but have not been developed for human use (FMOC-L-Leucine, described to be a PPARγ activator at the XIIth International Symposium Stockholm athersclerosis, retinoic acid, and 6-(6-hydroxy-5,5-dimethylhexyloxy)-2,2-dimethylhexyloxy)-2,2-dimethyl-hexan-1-ol); and (iii) compounds whose activity has been established in vitro but for which animal models have not yet been developed.

Using the multiplex HICS-FTMS screens described herein, peak profiles are of samples derived from cell contents and cell supernatants of cells individually exposed multiple members of each class of compounds described above, preferably in triplicate, preferably using different cell types and preferably each at a range of concentrations and a range of incubation periods for each compound.

The peak profiles within each class of compounds and among the classes of compounds are compared for each cell type.

Peaks that are commonly present in samples prepared from cells contacted for fibrates, glitazones and buiguanides are identified and characterized.

Peaks that are common for retinoic acid, esp 24232, FMOC-L-Leucine are identified and characterized.

Preferably, peaks are identified that are commonly present or absent in peak profiles of samples derived from cells treated with all three classes of drugs.

After common peaks are identified, experimental model animals (Zucker rats, diabetic rat model (streptozotocin injection), ob/ob mice, streptozotocin treated Syrian hamster (which do have CETP cholesterol ester transfer protein essential for HDL metabolism, present in man and absent in rats and mice)) are treated for 2 to 4 weeks with the different drugs, and blood samples are taken at different time points and analyzed by FTMS as described in Section 7, supra. Peaks in the different mass spectra are compared. Again, peaks common to all the drugs are characterized.

A collection of compounds (from combinatorial libraries and commercially available libraries) are incubated with different human cell lines (adipocytes, hepatocytes, enterocytes, muscles cells).

Cell content and supernatants are analyzed by FT-MS. Compounds that increase similar peaks as reference molecules in cells and animals are compared and structure activity relationships are determined. Molecules are compared suing computational chemistry software such as Catalyst (MSI). Pharmacophores are identified and hypotheses generated.

Hypothesis are then used to screen virtual library of compounds. The most active ones are then test in animals in an iterative process.

Testing pharmacophore/hypothesis generation synthesis of new chemical entities the most active compounds identified. Novel compounds identified in this manner are lead compounds for drug development.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

We claim:

1. A method for identifying one or more endogenous molecules that differ in abundance between a first cell population and a second cell population, comprising:
    (a) comparing a first Fourier Transform Mass Spectrometry (FTMS) peak profile obtained from the first cell population with a second FTMS peak profile obtained from the second cell population;
    (b) identifying one or more peaks that differ in intensity in the first FTMS peak profile relative to the second FTMS peak profile, which one or more peaks correspond to one or more molecules that differ in abundance between a first cell population and a second cell population; and
    (c) identifying said one or more said endogenals molecules that differ in abundance between a first cell population and a second cell population either directly from mass-to-charge (m/z) ratio or through additional fragmentation of said one or more molecules.

2. The method of claim 1, wherein the first and second cell populations do not contain a label.

3. The method of claim 1, further comprising:
    (c) prior to step (a), obtaining the first FTMS peak profile from the first cell population by subjecting said first cell population to FTMS.

4. The method of claim 1, further comprising:
    (c) prior to step (a), obtaining the second FTMS peak profile from the second cell population by subjecting said second cell population to FTMS.

5. The method of claim 3, further comprising:
    (d) prior to step (a), obtaining the second FTMS peak profile from the second cell population by subjecting said second cell population to FTMS.

6. The method of any one of claims 1–5, wherein the first cell population is a reference cell population and the second cell population is a test cell population.

7. The method of claim 6, wherein the first and second cell population are of different cell types.

8. The method of claim 7, wherein the first and second cell populations are of different tissue types from the same organism.

9. The method of claim 7, wherein the first and second cell populations are of the same tissue type from different organisms.

10. The method of claim 6, wherein the first and second cell populations are of the same cell type.

11. The method of claim 10, wherein the first cell population is a normal cell population, the second cell population is a diseased cell population and the one or more molecules are markers for the disease.

12. The method of claim 11, wherein the diseased cell population is a cancerous cell population and said markers are the markers for cancer.

13. The method of claim 12, wherein the cancerous cell population is a population of melanoma, myeloid leukemia, or carcinoma cells.

14. The method of claim 13, wherein the carcinoma is lung, breast, ovarian, colon, kidney, prostate, pancreatic, stomach, brain, lymphatic system, thymic, thyroid, adrenal or testicular carcinoma.

15. The method of claim 11, wherein the diseased cell population is from an individual with cardiovascular disease and said markers are the markers for cardiovascular disease.

16. The method of claim 15, wherein the diseased cell population is a population of cardiomyocytes, endothelial cells, macrophages, hepatocytes, adipocytes, smooth muscle cells or intestinal cells.

17. The method of claim 11, wherein the diseased cell population is from an individual with diabetes and said markers are the markers for diabetes.

18. The method of claim 17, wherein the diseased cell population is a population of cardiomyocytes, endothelial cells, macrophages, pancreatic cells, hepatocytes, adipocytes, smooth muscle cells or intestinal cells.

19. The method of claim 11, wherein the diseased cell population is from an obese individual.

20. The method of claim 19, wherein the diseased cell population is a population of cardiomyocytes, endothelial cells, macrophages, hepatocytes, adipocytes, smooth muscle cells or intestinal cells.

21. The method of claim 10, wherein the first cell population has not been subjected to a test agent and the second cell population has been subjected to the test agent.

22. The method of claim 21, wherein the test agent is a known drug.

23. The method of claim 21, wherein the test agent is a drug candidate.

24. The method of claim 21, wherein the test agent is a small molecule.

25. The method of claim 21, wherein the test agent is a protein.

26. The method of claim 25, wherein the protein is a hormone, a growth factor, a cytokine, a ligand, or an antibody.

27. The method of claim 21, wherein the test agent is a nucleic acid.

28. The method of claim 27, wherein the nucleic acid is a DNA, an RNA, or a DNA-RNA hybrid.

29. The method of claim 6, wherein the first FTMS peak profile is a historical control.

30. The method of claim 6, wherein the first FTMS peak profile is a concurrent control.

31. The method of any one of claims 1–5, wherein the first and second cell populations are populations of primary cells from a tissue or organ.

32. The method of claim 31, wherein in the primary cells are primary brain, skin, lung, endothelial, epithelial, adipose, muscle, bone, stomach, colon, spleen, pancreas, kidney, bladder, heart, lymphatic system, blood, or liver cells.

* * * * *